(12) United States Patent
Rivas et al.

(10) Patent No.: US 12,100,480 B2
(45) Date of Patent: Sep. 24, 2024

(54) ASSESSMENT OF POLYGENIC TRAIT RISK VIA TRAIT COMPONENTS AND APPLICATIONS THEREOF

(71) Applicant: The Board of Trustees of the Leland Stanford Junior University, Stanford, CA (US)

(72) Inventors: Manuel A. Rivas, Palo Alto, CA (US); Matthew Woodward Aguirre, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 511 days.

(21) Appl. No.: 17/005,241

(22) Filed: Aug. 27, 2020

(65) Prior Publication Data
US 2021/0065846 A1 Mar. 4, 2021

Related U.S. Application Data

(60) Provisional application No. 62/892,512, filed on Aug. 27, 2019.

(51) Int. Cl.
*G16B 20/20* (2019.01)
*C12Q 1/6883* (2018.01)

(52) U.S. Cl.
CPC .......... *G16B 20/20* (2019.02); *C12Q 1/6883* (2013.01); *C12Q 2600/156* (2013.01)

(58) Field of Classification Search
CPC . C12Q 1/6883; C12Q 2600/156; G16B 20/20
See application file for complete search history.

(56) References Cited

U.S. PATENT DOCUMENTS

| | | |
|---|---|---|
| 9,617,597 B2 | 4/2017 | Helgadottir et al. |
| 2018/0163262 A1 | 6/2018 | Behrens et al. |
| 2019/0017119 A1 | 1/2019 | Khera et al. |
| 2021/0123932 A1 | 4/2021 | Rivas et al. |

FOREIGN PATENT DOCUMENTS

| | | |
|---|---|---|
| CN | 109192316 A | 1/2019 |
| WO | 2016172764 A1 | 11/2016 |

OTHER PUBLICATIONS

Escott-Price V et al. Common polygenic variation enhances risk prediction for Alzheimer's disease. Brain. Dec. 2015;138(Pt 12):3673-84. doi: 10.1093/brain/awv268. Epub Oct. 21, 2015. PMID: 26490334; PMCID: PMC5006219. (Year: 2015).*
Escudero I, Johnstone M. Genetics of schizophrenia. Curr Psychiatry Rep. Nov. 2014;16(11):502. doi: 10.1007/s11920-014-0502-8 ( Year: 2014).*
Wightman et al. A genome-wide association study with 1,126,563 individuals identifies new risk loci for Alzheimer's disease. Nat Genet. Sep. 2021;53(9):1276-1282. doi: 10.1038/s41588-021-00921-z. Epub Sep. 7, 2021. Erratum in: Nat Genet. Dec. 2021;53(12):1722. Erratum in: Nat Genet. Jul. 2022;54(7):1062. (Year: 2021).*
Escott-Price V et al. Common polygenic variation enhances risk prediction for Alzheimer's disease. Brain. Dec. 2015;138(Pt 12):3673-84. doi: 10.1093/brain/awv268. Epub Oct. 21, 2015. PMID: 26490334; PMCID: PMC5006219. (Year: 2015) (Year: 2015).*
Escudero I, Johnstone M. Genetics of schizophrenia. Curr Psychiatry Rep. Nov. 2014;16(11):502. doi: 10.1007/s11920-014-0502-8 (Year: 2014) (Year: 2014).*
Wightman et al. A genome-wide association study with 1,126,563 individuals identifies new risk loci for Alzheimer's disease. Nat Genet. Sep. 2021;53(9):1276-1282. (Year: 2021).*
Duncan L, Shen H, Gelaye B, Meijsen J, Ressler K, Feldman M, Peterson R, Domingue B. Analysis of polygenic risk score usage and performance in diverse human populations. Nat Commun. Jul. 25, 2019;10(1):3328 (Year: 2019).*
Malik et al., "Low-frequency and common genetic variation in ischemic stroke: The METASTROKE collaboration", Neurology, vol. 87, No. 12, Sep. 20, 2016, pp. 1217-1226.
Marquez-Luna et al., "Multiethnic polygenic risk scores improve risk prediction in diverse populations", Genetic Epidemiology, vol. 41, No. 8, Dec. 2017, pp. 811-823.
Martin et al., "A Genetic Investigation of Sex Bias in the Prevalence of Attention-Deficit/Hyperactivity Disorder", Biological Psychiatry, 2017, vol. 83, pp. 1044-1053, https://doi.org/10.1016/j.biopsych.2017.11.026.
Mavaddat et al., "Polygenic Risk Scores for Prediction of Breast Cancer and Breast Cancer Subtypes", The American Journal of Human Genetics, vol. 104, No. 1, Jan. 3, 2019, pp. 21-34.
McCarthy, "Painting a new picture of personalised medicine for diabetes", Diabetologia, vol. 60, Feb. 7, 2017, pp. 793-799.
McInnes et al., "Global Biobank Engine: enabling genotype-phenotype browsing for biobank summary statistics", Bioinformatics, 2019. vol. 35, No. 14, pp. 2495-2497, Advance Access publication date Dec. 5, 2018, doi: 10.1093/bioinformatics/bty999.
Middelberg et al., "Genetic and Environmental Influences on Lipids, Lipoproteins, and Apolipoproteins", Arteriosclerosis, Thrombosis, and Vascular Biology, May 23, 2002, vol. 22, No. 7, pp. 1142-1147, https://doi.org/10.1161/01.ATV.0000022889.85440.79.
Morris et al., "Large-scale association analysis provides insights into the genetic architecture and pathophysiology of type 2 diabetes", Nature Genetics, vol. 44, Aug. 12, 2012, pp. 981-990.

(Continued)

*Primary Examiner* — Nancy J Leith
*Assistant Examiner* — Douglas Charles Ryan
(74) *Attorney, Agent, or Firm* — KPPB LLP

(57) ABSTRACT

Methods to determine an individual's propensity or risk for a trait and applications thereof are described. Generally, systems and methods utilize genetic data acquired from an individual to determine their propensity or risk for a set of components that contribute to a trait. Propensity or risk of a trait is determined by assessing propensity or risk for each component of a set of components and the weighted contribution of each component to the trait.

12 Claims, 17 Drawing Sheets
(16 of 17 Drawing Sheet(s) Filed in Color)

(56) References Cited

OTHER PUBLICATIONS

Ni et al., "Estimation of Genetic Correlation via Linkage Disequilibrium Score Regression and Genomic Restricted Maximum Likelihood", The American Journal of Human Genetics, Jun. 7, 2018. vol. 102, pp. 1185-1194, DOI: https://doi.org/10.1016/j.ajhg.2018.03.021.

Ober et al., "Sex-specific genetic architecture of human disease", Nat. Rev. Genet., Dec. 2008, vol. 9, No. 12, pp. 911-922, doi: 10.1038/nrg2415.

Paquette et al., "SLC22A3 is associated with lipoprotein (a) concentration and cardiovascular disease in familial hypercholesterolemia", Clinical Biochemistry, vol. 66, Apr. 2019, pp. 44-48.

Pei et al., "Tissue-specific enrichment analysis to decode tissue specificity", bioRxiv preprint, Nov. 9, 2018, 3 pgs., doi: https://doi.org/10.1101/456293.

Perry et al., "Parent-of-origin-specific allelic associations among 106 genomic loci for age at menarche", Nature, vol. 514, Jul. 23, 2014, pp. 92-97.

Pignatelli et al., "Androgens in Congenital Adrenal Hyperplasia", Front. Horm. Res., 2019, vol. 53, pp. 65-76, published online Sep. 9, 2019, doi: 10.1159/000494903.

Prescott et al., "Genome-Wide Association Study of Circulating Estradiol, Testosterone, and Sex Hormone-Binding Globulin in Postmenopausal Women", PLoS One, Jun. 2012, vol. 7, Issue 6, e37815, 8 pgs, published online Jun. 4, 2012, doi: 10.1371/journal.pone.0037815.

Pulit et al., "Meta-analysis of genome-wide association studies for body fat distribution in 694 649 individuals of European ancestry", Human Molecular Genetics, Jan. 1, 2019, vol. 28, No. 1, pp. 166-174. doi: 10.1093/hmg/ddy327.

Purcell et al., "PLINK: A Tool Set for Whole-Genome Association and Population-Based Linkage Analyses", The American Journal of Human Genetics, Sep. 2007, vol. 81, pp. 559-575, DOI: 10.1086/519795.

Qian et al., "A Fast and Flexible Algorithm for Solving the Lasso in Large-scale and Ultrahigh-dimensional Problems", bioRxiv, Retrieved from: https://www.biorxiv.org/content/10.1101/630079v1, May 7, 2019, 33 pgs.

Randall et al., "Sex-stratified Genome-wide Association Studies Including 270,000 Individuals Show Sexual Dimorphism in Genetic Loci for Anthropometric Traits", PLoS Genetics, Jun. 2013, vol. 9, Issue 6, e1003500, 19 pgs., doi: 10.1371/journal.pgen.1003500.

Rask-Andersen et al., "Genome-wide association study of body fat distribution identifies adiposity loci and sex-specific genetic effects", Nature Communications, Jan. 21, 2019, vol. 10, No. 339, doi,org/10.1038/s41467-018-08000-4.

Rawlik et al., "Evidence for sex-specific genetic architectures across a spectrum of human complex traits", Genome Biology, Jul. 29, 2016, vol. 17. No. 1, 8 pgs, DOI 10.1186/s13059-016-1025-x.

Ruth et al., "Using human genetics to understand the disease impacts of testosterone in men and women", Nature Medicine, vol. 26, Feb. 10, 2020, pp. 252-258.

Ryan et al., "Testosterone-Secreting Adrenal Adenoma That Contained Crystalloids of Reinke in an Adult Female Patient", Mayo Clinic Proceedings, Apr. 1, 1995, vol. 70, Issue 4, pp. 380-383, https://doi.org/10.4065/70.4.380.

Ryu et al., "Serum Uric Acid Levels and Cerebral Microbleeds in Patients with Acute Ischemic Stroke", PLoS One, vol. 8, No. 1, e55210, Jan. 2013, 6 pgs.

Schooling et al., "Genetic predictors of testosterone and their associations with cardiovascular disease and risk factors: A Mendelian randomization investigation", International Journal of Cardiology, Sep. 15, 2018, vol. 267. pp. 171-176, published online May 18, 2018. doi: 10.1016/j.ijcard.2018.05.051.

Schumacher et al., "Association analyses of more than 140,000 men identify 63 new prostate cancer susceptibility loci", Nature Genetics, vol. 50, Jun. 11, 2018, pp. 928-936.

Shungin et al., "New genetic loci link adipose and insulin biology to body fat distribution", Nature, vol. 518, Feb. 11, 2015, pp. 187-196.

Sinott-Armstrong et al., "Genetics of 38 blood and urine biomarkers in the UK Biobank", bioRxiv preprint, Jun. 5, 2019, 38 pgs., doi: https://doi.org/10.1101/660506.

Speed et al., "SumHer better estimates the SNP heritability of complex traits from summary statistics", Nat Genet. Feb. 2019. vol. 51, No. 2, pp. 277-284. doi: 10.1038/s41588-018-0279-5.

Stellato et al., "Testosterone, sex hormone-binding globulin, and the development of type 2 diabetes in middle-aged men: prospective results from the Massachusetts male aging study", Diabetes Care, Apr. 2000, vol. 23, No. 4, pp. 490-494, doi: 10.2337/diacare.23.4.490.

Stringer et al., "Author Correction: Majority of human traits do not show evidence for sex-specific genetic and environmental effects", Scientific Reports, vol. 8, 18060, Dec. 21, 2018, 1 pg.

Tanigawa et al., "Components of genetic associations across 2,138 phenotypes in the UK Biobank highlight novel adipocyte biology", bioRxiv, Retrieved from: https://www.biorxiv.org/content/10.1101/442715v2, Mar. 19, 2019, 61 pgs.

Vilhjalmsson et al., "Modeling Linkage Disequilibrium Increases Accuracy of Polygenic Risk Scores", The American Journal of Human Genetics, vol. 97, No. 4, Oct. 1, 2015, pp. 576-592.

Vitart et al., "SLC2A9 is a newly identified urate transporter influencing serum urate concentration, urate excretion and gout", Nature Genetics, vol. 40, Mar. 9, 2008, pp. 437-442.

Walker et al., "Using the MR-Base platform to investigate risk factors and drug targets for thousands of phenotypes", Wellcome Open Research, Jul. 2019, vol. 4, No. 113, DOI: 10. 12688/wellcomeopenres.15334.1.

Walters et al., "Exploring Sex Differences in the Genetics of UK Biobank Phenotypes", European Neuropsychopharmacology. 29. pp. S56, Jul. 2019, doi: 10.1016/j.euroneuro.2019.07.117.

Wells et al., "The anatomical distribution of genetic associations", Nucleic Acids Research, Dec. 15, 2015, vol. 43, No. 22, pp. 10804-10820, published online Nov. 19, 2015, doi: 10.1093/nar/gkv1262.

Winkler et al., "The Influence of Age and Sex on Genetic Associations with Adult Body Size and Shape: A Large-Scale Genome-Wide Interaction Study", PLOS Genetics, Oct. 1, 2015, vol. 11, No. 10, e1005378, 42 pgs., DOI: 10.1371/journal.pgen.1005378.

Wood et al., "Defining the role of common variation in the genomic and biological architecture of adult human height", Nature Genetics, vol. 46, Oct. 5, 2014, pp. 1173-1186.

Xu et al., "Cell Type-Specific Expression Analysis to Identify Putative Cellular Mechanisms for Neurogenetic Disorders", The Journal of Neuroscience, vol. 34, No. 4, Jan. 22, 2014, pp. 1420-1431.

Yamin et al., "Why Global Goals and Indicators Matter: The Experience of Sexual and Reproductive Health and Rights in the Millennium Development Goals", Journal of Human Development and Capabilities, 2014, vol. 15, No. 2 and 3, pp. 218-231, DOI: 10.1080/19452829.2014.896322.

Yang et al., "A new compound heterozygous mutation in a female with 17α-hydroxylase/17,20-lyase deficiency, slipped capital femoral epiphysis, and adrenal myelolipoma", Gynecol Endocrinol., May 2019, vol. 35, No. 5, pp. 385-389, published online Jan. 7, 2019, doi: 10.1080/09513590.2018.1540576.

Yang et al., "Concepts, estimation and interpretation of SNP-based heritability", Nature Genetics, Sep. 2017, vol. 49, No. 9, pp. 1304-1310, DOI: 10.1038/ng.3941.

Zachmann et al., "Testosterone treatment of excessively tall boys", The Journal of Pediatrics, vol. 88, No. 1, Jan. 1976, pp. 116-123.

Zhao et al., "A Mendelian randomization study of testosterone and cognition in men", Scientific Reports, Feb. 11, 2016, vol. 6, 21306, pp. 1-8, doi: 10.1038/srep21306.

Zhou et al., "A rare case of pure testosterone-secreting adrenal adenoma in a postmenopausal elderly woman", BMC Endocrine Disorders, Jan. 23, 2019, vol. 19, No. 14, 5 pgs., doi: 10.1186/s12902-019-0342-y.

"Global, regional, and national incidence, prevalence, and years lived with disability for 354 diseases and injuries for 195 countries

(56) References Cited

OTHER PUBLICATIONS and territories, 1990-2017: a systematic analysis for the Global Burden of Disease Study 2017", GBD 2017 Disease and Injury Incidence and Prevalence Collaborators, Global Health Metrics, vol. 392, No. 10159, Nov. 10, 2018, pp. 1789-1858.
Aguirre et al., "Phenome-wide Burden of Copy-Number Variation in the UK Biobank", The American Journal of Human Genetics, vol. 105, No. 2, Aug. 1, 2019, pp. 373-383, https://doi.org/10.1016/j.ajhg.2019.07.001.
Belsky et al., "Development and Evaluation of a Genetic Risk Score for Obesity", Biodemography and Social Biology, vol. 59, No. 1, May 23, 2013, pp. 85-100.
Bowden et al., "A framework for the investigation of pleiotropy in two-sample summary data Mendelian randomization", Statistics in Medicine, Jan. 23, 2017, vol. 36, pp. 1783-1802, DOI: 10.1002/sim.7221.
Bracken et al., "A high-volume, low-cost approach to participant screening and enrolment: Experiences from the T4DM diabetes prevention trial", Clinical Trials, Dec. 2019, vol. 16, No. 6, pp. 589-598, first published Oct. 3, 2019, doi: 10.1177/1740774519872999.
Brown et al., "Gene: a gene-centered information resource at NCBI", Nucleic Acids Research, vol. 43, Issue D1, Jan. 28, 2015, pp. D36-D42, published online Oct. 29, 2014, https://doi.org/10.1093/nar/gku1055.
Bulik-Sullivan, "Relationship between LD Score and Haseman-Elston Regression", bioRxiv preprint, 13 pgs., Apr. 19, 2015, doi: https://doi.org/10.1101/018283.
Bycroft et al., "The UK Biobank resource with deep phenotyping and genomic data", Nature, vol. 562, Oct. 10, 2018, pp. 203-209, https://doi.org/10.1038/s41586-018-0579-z.
Carpenter et al., "Stan: A Probabilistic Programming Language", Journal of Statistical Software, Jan. 2017, vol. 76, Issue 1, pp. 1-32, DOI: 10.18637/jss.v076.i01.
Chang et al., "Second-generation PLINK: rising to the challenge of larger and richer datasets", GigaScience, 2015, vol. 4, No. 7, published online Feb. 25, 2015, 16 pgs., DOI: 10.1186/s137742-015-0047-8.
Dankers et al., "Hyperuricemia influences tryptophan metabolism via inhibition of multidrug resistance protein 4 (MRP4) and breast cancer resistance protein (BCRP)", Biochimica et Biophysica Acta (BBA)—Molecular Basis of Disease, vol. 1832, No. 10, Oct. 2013, pp. 1715-1722.
Deboever et al., "Medical relevance of protein-truncating variants across 337,205 individuals in the UK Biobank study", Nature Communications, vol. 9, No. 1612, Apr. 24, 2018, 10 pgs., doi: 10.1038/s41467-018-03910-9.
Deloukas et al., "Large-scale association analysis identifies new risk loci for coronary artery disease", The CARDIoGRAMplusC4D Consortium, Nature Genetics, vol. 45, Dec. 2, 2012, pp. 25-33.
Dougherty et al., "Analytical approaches to RNA profiling data for the identification of genes enriched in specific cells", Nucleic Acids Research, Mar. 22, 2010, vol. 38, No. 13, pp. 4218-4230, DOI: 10.1093/nar/gkq130.
Eriksson et al., "Causal relationship between obesity and serum testosterone status in men: A bi-directional mendelian randomization analysis", PLoS One, Apr. 27, 2017, vol. 12, No. 4, e0176277, 15pgs., doi: 10.1371/journal.pone.0176277.
Euesden et al., "PRSice: Polygenic Risk Score software", Bioinformatics, vol. 31, No. 9, May 1, 2015, pp. 1466-1468.
Frayling et al., "A Common Variant in the FTO Gene Is Associated with Body Mass Index and Predisposes to Childhood and Adult Obesity", Science, vol. 316, No. 5826, May 11, 2007, pp. 889-894.
Fritsche et al., "Association of Polygenic Risk Scores for Multiple Cancers in a Phenome-wide Study: Results from The Michigan Genomics Initiative", The American Journal of Human Genetics, vol. 102, No. 6, Jun. 7, 2018, pp. 1048-1061.
Gamazon et al., "SNP-based heritability estimation: measurement noise, population stratification and stability", bioRxiv preprint, 18 pgs., Mar. 8, 2016, doi: https://doi.org/10.1101/040055.

Gianatti et al., "Effect of testosterone treatment on glucose metabolism in men with type 2 diabetes: a randomized controlled trial", Diabetes Care, Aug. 2014, vol. 37, No. 8, pp. 2098-2107, doi: 10.2337/dc13-2845.
Gonzalez et al., "Editorial: Management of Females with Congenital Adrenal Hyperplasia", Frontiers in Pediatrics, Dec. 22, 2017, vol. 5, Article 282, 2 pgs., doi: 10.3389/fped.2017.00282.
Groß et al., "High frequency of mutations in the CYP21 gene in patients with suspected adrenal enzyme deficiencies and hirsutism", Experimental and Clinical Endocrinology & Diabetes, 2004, vol. 12, doi:10.1055/s-2004-819293.
Halko et al., "Finding Structure with Randomness: Probabilistic Algorithms for Constructing Approximate Matrix Decompositions", SIAM Review, vol. 53, No. 2, May 5, 2011, pp. 217-288.
Handelsman et al., "Age-specific population centiles for androgen status in men", European Journal of Endocrinology, vol. 173, No. 6, Dec. 2015, pp. 809-817.
Haring et al., "Prospective association of low total testosterone concentrations with an adverse lipid profile and increased incident dyslipidemia", European Journal of Cardiovascular Prevention & Rehabilitation, vol. 18, No. 1, Feb. 2011, pp. 86-96.
Heid et al., "Meta-analysis identifies 13 new loci associated with waist-hip ratio and reveals sexual dimorphism in the genetic basis of fat distribution". Nat. Genetics, Nov. 2010, vol. 42, No. 11, pp. 949-960, doi: 10.1038/ng.685.
Hemani et al., "The MR-Base platform supports systematic causal inference across the human phenome", Elife, May 30, 2018, vol. 7, e34408, 29 pgs., doi: 10.7554/eLife.34408.
Hill, "Estimation of heritability by regression using collateral relatives: linear heritability estimation", Genetical Research, 1978, vol. 32, pp. 265-274.
Kelemen et al., "Linkage analysis of obesity phenotypes in pre- and post-menopausal women from a United States mid-western population", BMC Medical Genetics, 2010, vol. 11, No. 156, 9 pgs., http://www.biomedcentral.com/1471-2350/11/156.
Khera et al., "Genome-wide polygenic scores for common diseases identify individuals with risk equivalent to monogenic mutations", Nature Genetics, vol. 50, Aug. 13, 2018, pp. 1219-1224.
Khera et al., "Polygenic Prediction of Weight and Obesity Trajectories from Birth to Adulthood", Cell, vol. 177, No. 3, Apr. 18, 2019, pp. 587-596.e9.
Khera et al., "Whole-Genome Sequencing to Characterize Monogenic and Polygenic Contributions in Patients Hospitalized With Early-Onset Myocardial Infarction", Circulation, vol. 139, No. 13, Mar. 26, 2019, pp. 1593-1602.
Khramtsova et al., "The role of sex in the genomics of human complex traits", Nature Reviews Genetics, vol. 20, Dec. 23, 2018, pp. 173-190.
Kim et al., "Polycystic ovary syndrome with hyperandrogenism as a risk factor for non-obese non-alcoholic fatty liver disease", Alimentary Pharmacology & Therapeutics, vol. 45, No. 11, Mar. 29, 2017, pp. 1403-1412.
Kottgen et al., "Multiple Loci Associated With Indices of Renal Function And Chronic Kidney Disease", Nature Genetics, vol. 41, May 10, 2009, pp. 712-717.
Kuleshov et al., "Enrichr: a comprehensive gene set enrichment analysis web server 2016 update", Nucleic Acids Research, Jul. 8, 2016, vol. 44, Web Server issue, pp. W90-W97, published online May 3, 2016, doi: 10.1093/nar/gkw377.
Kuo et al., "Familial aggregation of gout and relative genetic and environmental contributions: a nationwide population study in Taiwan", Annals of the Rheumatic Diseases, vol. 74, No. 2, Nov. 21, 2013, pp. 369-374.
Lall et al., "Personalized risk prediction for type 2 diabetes: the potential of genetic risk scores", Genetics in Medicine, vol. 19, Aug. 11, 2016, pp. 322-329.
Liu et al., "Cloning of two candidate tumor suppressor genes within a 10 kb region on chromosome 13q14, frequently deleted in chronic lymphocytic leukemia", Oncogene, vol. 15, Nov. 13, 1997, pp. 2463-2473.
Locke et al., "Genetic studies of body mass index yield new insights for obesity biology", Nature, vol. 518, Feb. 11, 2015, pp. 197-206.

(56) References Cited

OTHER PUBLICATIONS

Luo et al., "Association of genetically predicted testosterone with thromboembolism, heart failure, and myocardial infarction: mendelian randomisation study in UK Biobank", BMJ, Mar. 6, 2019, vol. 364, No. 476, pp. 1-8, doi: 10.1136/bmj.l476.

Mack et al., "A genome-wide association meta-analysis on lipoprotein (a) concentrations adjusted for apolipoprotein (a) isoforms", Journal of Lipid Research, vol. 58, Sep. 2017, pp. 1834-1844.

Antonio et al., "Associations Between Sex Steroids and the Development of Metabolic Syndrome: A Longitudinal Study in European Men", The Journal of Clinical Endocrinology & Metabolism, Apr. 1, 2015, vol. 100, Issue 4, pp. 1396-1404, https://doi.org/10.1210/jc.2014-4184.

Corona et al., "Therapy of Endocrine Disease: Testosterone supplementation and body composition: results from a meta-analysis study", European Journal of Endocrinology, Mar. 2016, vol. 174, Issue 3, R99-R116, DOI: https://doi.org/10.1530/EJE-15-0262.

Olson et al., "Variants in Estrogen Biosynthesis Genes, Sex Steroid Hormone Levels, and Endometrial Cancer: A Huge Review", American Journal of Epidemiology, Nov. 16, 2006, vol. 165, No. 3.

Pedregosa et al., "Scikit-learn: Machine Learning in Python", Journal of Machine Learning Research, Oct. 2011, vol. 12, pp. 2825-2830.

Tibshirani et al., "Estimating the number of clusters in a data set via the gap statistic", J. R. Statist. Soc. B, 2001, vol. 63, Part 2, pp. 411-423.

\* cited by examiner

ASSESSMENT OF POLYGENIC TRAIT RISK VIA TRAIT COMPONENTS AND APPLICATIONS THEREOF

CROSS REFERENCE TO RELATED APPLICATIONS

This application claims priority to U.S. Provisional Application Ser. No. 62/892,512, entitled "Polygenic risk modeling with latent trait-related genetic components," by Manuel A. Rivas et al., filed Aug. 27, 2019, which is incorporated herein by reference in its entirety.

STATEMENT REGARDING FEDERALLY SPONSORED RESEARCH OR DEVELOPMENT

This invention was made with Government support under contract HG010140 awarded by the National Institutes of Health. The Government has certain rights in the invention.

TECHNICAL FIELD

The invention is generally directed toward methods and systems to assess polygenic trait risk, and more specifically directed towards methods to assess polygenic trait risk via a set of components of the trait and various applications thereof.

BACKGROUND

In genetics, a genome-wide association study (GWAS) is an observational study of a genome-wide set of genetic variants in different individuals to see if any variant is associated with a trait. Genetic variants are differences gene sequence at a particular location within the genome. Genetic variants include single nucleotide variants (SNVs), insertions, deletions, and copy number variants (CNVs).

SNVs, also referred to as single nucleotide polymorphisms (SNPs), are differences of a single nucleotide at a particular location. There are four nucleotides in DNA: adenine (A), cytosine (C), guanine (G), and thymine (T). Thus, one individual's may have an adenine (A) at a particular nucleotide position in their DNA and a second individual may have a cytosine (C) at a particular nucleotide position in their DNA; and collectively this difference is a SNV.

An insertion is the addition of nucleotides at a particular location whereas a deletion is the removal of nucleotides at a particular location. A CNV is when a particular DNA sequence has multiple copies and differences in copy number varies from one individual to another. For example, an individual may have two copies of a particular gene whereas a second individual may have three copies of a particular gene.

Variations in DNA sequence, whether an SNV, insertion, deletion, or CNV, gives rise to variations in human traits, including benign traits (e.g., eye color) and medical disorders (e.g., obesity). Thus, one individual may have higher propensity or risk for a particular trait than a second individual due to the differences in the DNA variants between the individuals.

SUMMARY

Various embodiments are directed systems and methods for assessing polygenic risk. In various embodiments, an individual's genetic data is collected and assessed to determine propensity and/or risk of a trait. In various embodiments, an individual's propensity and/or risk of a trait is based on the individual's propensity and/or risk for a set of components that contribute to the trait. In various embodiments, a polygenic risk assessment is utilized to provide a medically related intervention and/or treat the individual accordingly.

In an embodiment, an individual's risk is determined for a medical disorder for treatment or further diagnostic assessment. Genetic sequence data comprising variants of an individual is obtained. For a medical disorder, a component polygenic risk score is determined for each component of a set of components. Utilizing the set of component polygenic risk scores, a comprehensive polygenic score is determined for the medical disorder. The comprehensive polygenic score indicates the individual is likely to have or to develop the medical disorder. Based on the comprehensive polygenic score, a treatment is performed on individual for the medical disorder or a diagnostic is performed on the individual to further assess the medical disorder.

In another embodiment, the contribution of a number of components of the set of components is determined. The contribution of at least one component indicates that the at least one component is a factor involved in manifestation of the polygenic disorder. The performing the treatment or the performing the diagnostic is directed towards the at least one component based on the contribution of the at least one component.

In yet another embodiment, the components that assessed for contribution have the same sign as the comprehensive polygenic risk score.

In a further embodiment, a biopsy of the individual is obtained. DNA is extracted from the biopsy. The extracted DNA is sequenced to yield the genetic sequence data.

In still yet another embodiment, the variants include single nucleotide variants, insertions, deletions, copy number variants, or HLA alleles.

In yet a further embodiment, the medical disorder is Alzheimer's disease, arthritis, asthma, coronary artery disease, Crohn's disease, dementia, diabetes, heart disease, heart failure, cholesterol imbalance, hypertension, hypothyroidism, irritable bowel syndrome, obesity, Parkinson's disease, psoriasis, sleep apnea, or stroke.

In an even further embodiment, the number of components in the set of components is an integer between 50 and 500.

In yet an even further embodiment, the number of components is 500.

In still yet an even further embodiment, the set of components is determined by decomposing the genetic associations of the medical disorder by determining associations between the variants and underlying or related traits.

In still yet an even further embodiment, a truncated singular value decomposition is utilized to identify the set of components.

In still yet an even further embodiment, each component polygenic risk score is computed by assuming variants make additive contributions.

In still yet an even further embodiment, the comprehensive polygenic score is determined by aggregating each component polygenic risk score of the set of components.

In still yet an even further embodiment, each component polygenic risk score of the set of components is computed using genome wide association beta or z-statistics.

In still yet an even further embodiment, the comprehensive polygenic risk score is adjusted by age, sex, genetic principal components, or any combination thereof.

In still yet an even further embodiment, the adjustment is performed by fitting a multiple regression model with polygenic risk scores and covariates in a validation population.

In still yet an even further embodiment, the comprehensive polygenic risk score is above a threshold.

In still yet an even further embodiment, the threshold is determined empirically to capture a certain percentage of individual having the medical disorder in a population.

In an embodiment, an individual's propensity for a polygenic trait is determined. For a polygenic train, a component polygenic risk score is determined for each component of a set of components. Utilizing the set of component polygenic risk scores, a comprehensive polygenic score is determined for the trait.

In another embodiment, the set of components is determined by decomposing the genetic associations of the trait by determining associations between the variants and underlying or related traits.

In yet another embodiment, a truncated singular value decomposition is utilized to identify the set of components.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The description and claims will be more fully understood with reference to the following figures and data graphs, which are presented as exemplary embodiments of the invention and should not be construed as a complete recitation of the scope of the invention.

FIG. 2 further provides an example of component polygenic risk scores (cPRS) is performed by taking the truncated singular value decomposition (TSVD) of a matrix W(n×m) containing summary statistics from GWAS of n=977 traits over m=469,341 variants from the UK Biobank. The squared columns of the resulting singular matrices U (n×c) and V (m×c) measure the importance of traits (variants) to each component; the rows map traits (variants) back to components. The squared cosine score (a unit-normalized row of US) for some hypothetical trait indicates high contribution from PC1, PC4, and PC5, utilized in accordance with various embodiments.

FIG. 8 further provides receiver operating curves with area under curve (AUC) values for MI or gout for dPRS, PRS, covariates, and a joint model with covariates and dPRS. Models with covariates were fit in the validation set; all evaluation was in the test set.

DETAILED DESCRIPTION

Figure 1:
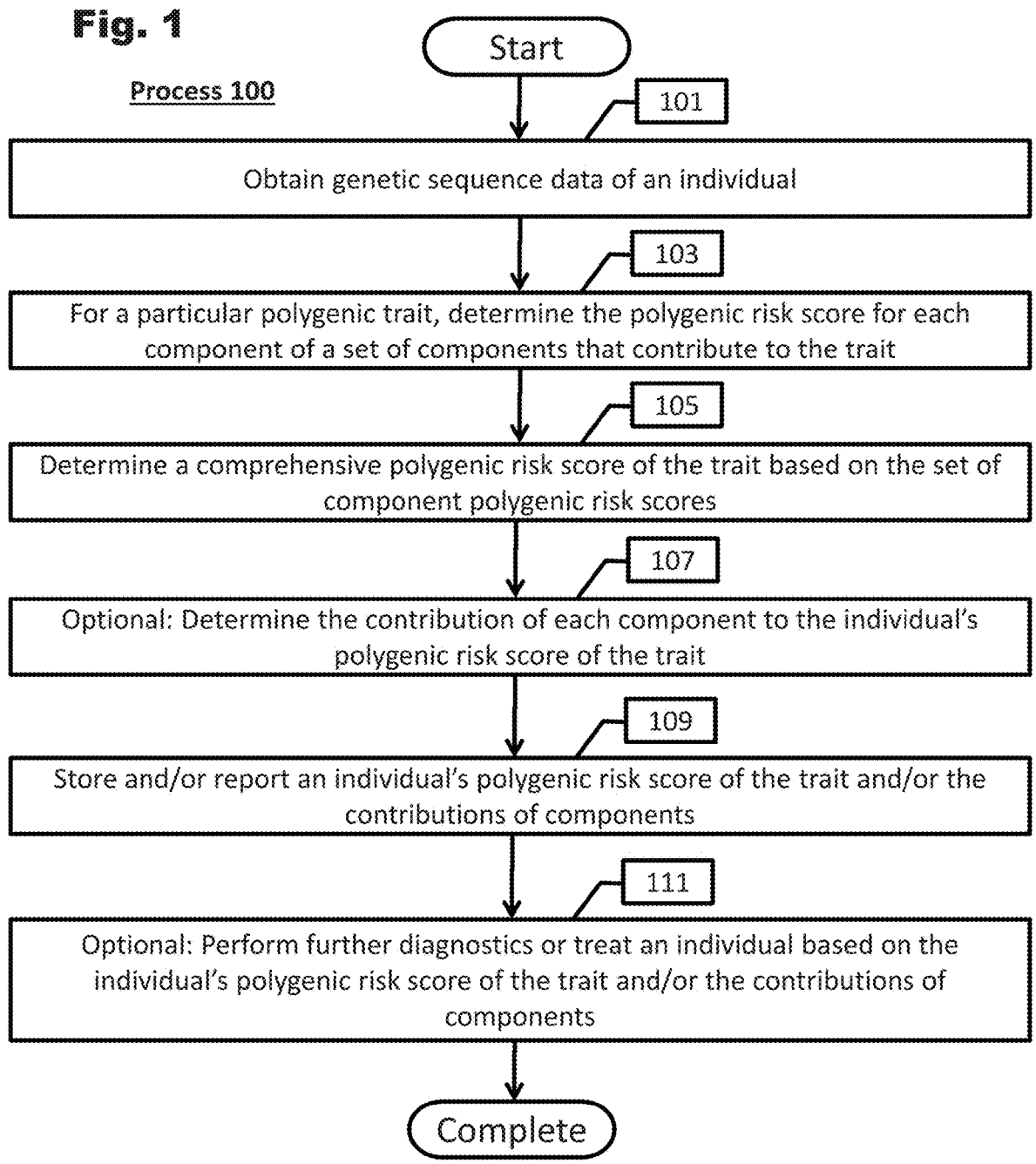
FIG. 1 provides a flow chart of a method to determine an individual's polygenic risk score of a particular trait, the contributions of each component within a set of components to a particular trait, and/or an individual's risk for a particular trait, in accordance with various embodiments.

Turning now to the drawings and data, systems and methods for assessing polygenic risks and/or propensities for a trait are provided, in accordance with various embodiments. In several embodiments, a trait is assessed by decomposing the trait into a set of components that contribute to the trait. In several embodiments, the genetic data of individual is utilized to determine the individual's risk and/or propensity for each component of the set of components that contribute to the trait. In several embodiments, an individual's comprehensive risk and/or propensity for the trait is determined based on the risk and/or propensity of each component of the set of components that contribute to the trait. In several embodiments, an individual's risk and/or propensity for a trait is determined utilizing a subset of components. Further, in several embodiments, the contribution of each component to an individual's comprehensive risk and/or propensity for the trait is determined, which may yield insight into the underlying and/or related factors that give rise to an individual's or group of individuals' comprehensive risk and/or propensity for the trait. In several embodiments, further diagnostics and or treatments may be performed on the individual based on the individual's risk and/or propensity for the trait and/or component contribution.

Generally, the various embodiments described herein provide a number of benefits within the realm of diagnostics and treatments. Of first order, because in various embodiments traits are decomposed into components and further assessed based upon its components, these various embodiments provide a highly intricate assessment of traits. This high intricacy can provide a better overall assessment of risk and/or propensity of traits. Further, in various embodiments, the components that contribute to risk are assessed for their contribution to an individual's risk and/or propensity of a trait. Accordingly, the underlying pathology of an individual's risk and/or propensity of a trait is determinable and can better inform further diagnostics and/or treatments. For example, an individual's risk for heart disease can be determined, and heart disease would be decomposed into a number of polygenic components such as (for example) cholesterol levels/ratios, obesity, glycemia, triglyceride levels, hypertension, etc. In accordance with various embodiments, the contribution each component to the risk heart disease is determined and thus provides insight on which underlying and/or related factors are contributing the most to the risk. Accordingly, in various embodiments, particular components are prioritized for further diagnostic assessment and/or specifically treated based on their contribution. For instance, if an individual has an elevated risk for heart disease and glycemia and hypertension are determined to be high contributors to heart disease risk but cholesterol levels/ratios were found to be a low contributor or even protective, further specific diagnostics and treatments on glycemia and hypertension can be prioritized, whereas diagnostics and treatments on cholesterol levels/ratios can be given less priority or even passed over.

It is noted that various embodiments described herein can be utilized to determine the risk and/or propensity of developing or having a trait. Although the term "risk" is generally related to developing or having a negative trait (e.g., medical disorder) and likewise the term "propensity" is generally related to developing or having a benign trait (e.g., eye color), the terms "risk" and "propensity" should not be held to these strict definitions. Accordingly, throughout the description herein, the terms "risk" and "propensity" are used interchangeably as it relates to a trait generally, and whether the trait has negative, positive, or benign association.

Polygenic Risk Assessment

A conceptual illustration of process for determining an individual's risk for a trait using their genetic data, in accordance with various embodiments is shown in FIG. 1. This process is directed to determining an individual's risk score for each component of a set of components that contribute to the trait. Once risk score for each component is determined, in some embodiments, the individual's overall score for is determined. In some embodiments, risk is determined utilizing only a subset of components. In some embodiments, the contribution of each component to the individual's overall trait risk is determined. And in some embodiments, further diagnostics and/or treatments is performed on the individual based on the individual's polygenic risk/propensity score of the trait and/or the contributions of each component.

As shown in FIG. 1, Process 100 obtains (101) an individual's genetic sequence data. The data, in accordance with many embodiments, is any DNA sequence data of individual that is inclusive of genetic variants to be analyzed. In some embodiments, genetic data is an individual's whole genome, a partial genome, or other data that is directed towards the regions of an individual's sequence and is inclusive of variant data. In some embodiments, genetic data is only sequencing data on a set of loci that have been found to be important to the trait to be analyzed (e.g., capture sequencing). Variants to be assessed, in accordance with various embodiments, are to include SNVs, insertions, deletions, CNVs, or any combinations thereof. In some embodiments, sequence data are obtained by a biopsy of an individual, in which genetic material is extracted and sequenced.

In accordance with various embodiments, an individual's genetic sequence data are processed to identify variants. In many embodiments, an individual's set of variants is further analyzed and trimmed, often dependent on the application. In some embodiments, variants of a particular frequency (e.g., rare variants with MAF≤1.0%) are excluded.

For a particular polygenic trait, a polygenic risk score is determined (103) for each component of a set of components that contribute to the manifestation of the trait. A component, in accordance with various embodiments, is a contribution in the trait. In some embodiments, components of a trait are determined by decomposing the genetic associations of the trait by determining associations between genetic variants and related traits. Any appropriate number of components can be utilized. In various embodiments, any integer between 50 and 500 genetic components are utilized. In some embodiments, a truncated singular value decomposition (TSVD) is utilized identify the top set of components for analysis. Accordingly, in some embodiments, decomposition results in a matrix of singular traits, a matrix of singular variants, and a diagonal matrix of singular matrix for each component.

In some embodiments, to determine a polygenic risk score of a component, in some embodiments, the matrix of singular traits, the matrix of singular variants, and the diagonal matrix are utilized. In some embodiments, a component polygenic risk score is computed by assuming variants and/or alleles make additive contributions across sites. In some embodiments, polygenic risk score is computed by centering each component to zero.

Based on the polygenic risk scores of each component the set of components that contribute to the trait, a comprehensive polygenic risk score is determined (105) of the trait. In some embodiments, each component polygenic risk score is aggregated to determine a comprehensive polygenic risk score. In some embodiments, the population distribution of the comprehensive polygenic risk score for each trait is scaled to zero mean and unit variance. In various embodiments, a comprehensive polygenic risk score is adjusted by age, sex, genetic principal components, or any combination thereof. In some embodiments, adjustment is performed by fitting a multiple regression model with polygenic risk scores and covariates in a validation population.

In some embodiments, a comprehensive polygenic risk score is used to determine whether a particular trait is likely to manifest. In some embodiments, a threshold is used to determine whether a comprehensive polygenic risk score will result in a trait. In some embodiments, comprehensive polygenic risk score is used to diagnose an individual for a trait (e.g., medical disorder). comprehensive polygenic risk scores can be especially useful to diagnose polygenic diseases that may arise from genetic variants, such as (for example) Alzheimer's disease, arthritis, asthma, coronary artery disease, Crohn's disease, dementia, diabetes, heart disease, heart failure, cholesterol imbalance, hypertension, hypothyroidism, irritable bowel syndrome, obesity, Parkinson's disease, psoriasis, sleep apnea, and stroke.

In some embodiments, hyperparameters of a comprehensive polygenic risk score model are optimized and selected. In various embodiments, GWAS beta, z-statistics, or a combination thereof are utilized as weights for a polygenic risk model. In some embodiments, a rank correlation is computed between comprehensive polygenic risk scores and covariate-adjusted trait residuals in training and/or validation data sets. In some embodiments, a correlation threshold between training and validation set performance is utilized to avoid overfitting. In some embodiments, a receiver operating curve (AUROC/AUC) is determined to assess model's ability to predict a polygenic risk score.

In some embodiments, the contribution of each component, of the set of components, to the comprehensive polygenic risk scores of the trait is determined (107). In some embodiments, the contribution of each component to an individual's comprehensive polygenic risk score, only component scores which have the same sign as the overall risk score are considered. This gives normalized risk profiles consisting of driving components for high risk individuals with positive comprehensive polygenic risk score and protective components for low risk individuals with negative comprehensive polygenic risk score.

An individual's polygenic risk score of the trait and/or the contributions of each component are stored and/or reported (109). In a number of embodiments, based on an individual's polygenic risk score of the trait, the contributions of each component, and/or an individual's risk profile, further diagnoses and/or treatments are performed (111) on the individual.

While specific examples of determining an individual's risk for a trait are described above, one of ordinary skill in the art can appreciate that various steps of the process can be performed in different orders and that certain steps may be optional according to some embodiments of the invention. As such, it should be clear that the various steps of the process could be used as appropriate to the requirements of specific applications.

Acquiring Genetic Data

In several embodiments, genetic data to be obtained can be any sequence data that contain genetic variants. In several embodiments, genetic data are full or partial genomes; in some embodiments, genetic data are full or partial exomes. Whole genomes may be preferred when it would be beneficial to identify variants in intronic and intergenic regions in addition to exonic regions. In some embodiments, exome data, covering the coding sequences of the genome, will suffice, as these data likely include a substantial portion of the variants related to a particular trait.

In accordance with various embodiments, genetic data can be derived from a number of sources. In some embodiments, these sources include sequences derived from DNA of a biological source that are subsequently processed and sequenced. In other embodiments, sequences are obtained from a publicly or privately available database. Many databases exist that store datasets of sequences from which a user can extract the data to perform experiments upon.

In some embodiments, de novo biological samples of DNA can be used for sequencing that are each derived from a biopsy of an individual. In particular embodiments, the DNA to be acquired can be derived from biopsies of human patients associated with a phenotype or a disease state. Any appropriate biopsy containing a sufficient amount of an individual's DNA can be utilized, such as (for example), blood extraction, skin puncture, surgical extraction of tissue, and/or body excretions (e.g., saliva, mucus, urine, and stool).

In some embodiments, the DNA can be derived from common research sources, such as in vitro tissue culture cell lines or research mouse models. In many embodiments involving de novo extraction, the DNA molecules are extracted, processed and sequenced according to methods commonly understood in the field.

Regardless of the source of sequencing data, in a number of embodiments, variants are identified from sequencing data that has a large amount of coverage. In some embodiments, 5×, 10×, 20×, 30×, 40×, 50×, or >50× coverage is performed. In many embodiments, more coverage reduces sequencing error.

In several embodiments, an individual's set of variants is analyzed and trimmed. In some embodiments, variants indicating unreliable genotyping are removed, such as having a high missingness (e.g., >1%) or being a gross departure ($p<10^{-7}$) from Hardy-Weinberg Equilibrium. In some embodiments, synonymous variants are removed due to the fact that these variants are unlikely to have an effect on a trait. In some embodiments, only particular subsets of variants are analyzed. For example, in some embodiments, only SNVs, insertions, deletions, CNVs, HLA allelotypes, or a combination thereof, are analyzed. In some embodiments, only variants of a particular frequency (e.g., variants with MAF>0.01%) are examined and thus all other variants are excluded. In some embodiments, linkage disequilibrium (LD) score is utilized to filter variants. In some embodiments, known and/or pre-classified variants from known various databases are removed. For example, when examining variants related to a disorder, it may be ideal to remove known variants that exist in databases of healthy individuals, as it may be reasonable to presume that these variants are not related to a disordered state.

Applications Utilizing Polygenic Risk Score

Various embodiments are directed to performing diagnostics and treatments upon individuals based on their trait risk. As described herein, an individual may be determined as having a particular trait risk in relation to a disease. In some embodiments, an individual is diagnosed as having a disorder or having a high propensity for a disorder. In some embodiments, the contribution of various components to a particular trait risk is utilized to infer further diagnostics and/or treatments.

Diagnostic Methods

A number of embodiments are directed towards diagnosing individuals using polygenic risk score for a trait. In some embodiments, a trained polygenic risk model has been trained to determine an individual's polygenic risk score for a particular medical disorder.

In several of embodiments, initial diagnostics can be performed as follows:
 obtain genetic data of the individual to be diagnosed
 determine, utilizing a computational model, a polygenic risk score for a trait based on the components that contribute to the trait
 diagnose the individual based on the polygenic risk score.

Diagnoses, in accordance with various embodiments, can be performed as portrayed and described in FIG. 1. In some embodiments, a diagnosis is based on a polygenic risk score being equal to and/or above a threshold. A threshold can be determined by any appropriate means. In some embodiments, a threshold is determined empirically, such as a threshold that captures a certain percentage of individuals having a particular disorder as assessed within a population. It is to be understood that a threshold can be set to be more sensitive (i.e., capturing more individuals that develop or have a medical disorder but may include false positives) or more specific (i.e., capturing less individuals that develop or have a medical disorder and thus may exclude false negatives). Accordingly, in some embodiments a threshold is set to capture at least 99%, 95%, 90%, 85%, 80%, 75%, 70%, 65% 60%, 55%, or 50% of individuals developing or having a particular disorder.

In several of embodiments, initial diagnostics can be performed as follows:
 obtain genetic data of the individual to be diagnosed
 determine, utilizing a computational model, a polygenic risk score for a trait based on the components that contribute to the trait
 determine, utilizing a computational model, the contribution of a number of components that give rise to the polygenic risk score
 diagnose the individual based on the contribution of a number of components.

Diagnoses, in accordance with various embodiments, can be performed as portrayed and described in FIG. 1. In some embodiments, a diagnosis is based on a component contribution being equal to and/or above a threshold. A threshold can be determined by any appropriate means. In some embodiments, a threshold is determined empirically, such as a threshold that captures a certain percentage of individuals developing or having a particular disorder based on component contribution as assessed within a population. It is to be understood that a threshold can be set to be more sensitive (i.e., capturing more individuals that develop or have a medical disorder but may include false positives) or more specific (i.e., capturing less individuals that develop or have a medical disorder and thus may exclude false negatives). Accordingly, in some embodiments a threshold is set to capture at least 99%, 95%, 90%, 85%, 80%, 75%, 70%, 65% 60%, 55%, or 50% of individuals developing or having a particular disorder based on component contribution.

Many embodiments of diagnostics improve on traditional diagnostic methods, especially in cases of polygenic disorders. Because the genetic contribution to polygenic disorders is often obscured by lack of understanding the intricacies of the underlying and/or related factors that give rise to the disorder. As described herein, however, in some embodiments, a diagnosis is performed for a polygenic disease utilizing decomposition of traits into components, such as described in FIG. 1. In some embodiments, diagnoses are performed for disorders in which no single variant is diagnostic. In some embodiments, diagnoses are performed for disorders that arise at least in part by variants that affect the contribution of one or more components. Various embodiments are directed to diagnoses of polygenic (i.e., multifactorial) traits, including (but not limited to) Alzheimer's disease, arthritis, asthma, coronary artery disease, Crohn's disease, dementia, diabetes, heart disease, heart failure, cholesterol imbalance, hypertension, hypothyroidism, irritable bowel syndrome, obesity, Parkinson's disease, psoriasis, sleep apnea, and stroke.

Medications, Supplements, and Further Diagnostics

Several embodiments are directed to the use of medications and/or dietary supplements to treat an individual in based upon a polygenic risk and/or component contribution assessment. Likewise, several embodiments are directed to performing further diagnostics in response to a polygenic risk and/or component contribution assessment.

In some embodiments, medications and/or dietary supplements are administered in a therapeutically effective amount as part of a course of treatment. As used in this context, to "treat" means to ameliorate at least one symptom of the disorder to be treated or to provide a beneficial physiological effect.

A therapeutically effective amount can be an amount sufficient to prevent reduce, ameliorate or eliminate symptoms of disorders or pathological conditions susceptible to such treatment, such as (for example) obesity, myocardial infarction, gout, heart disease, or other polygenic diseases. In some embodiments, a therapeutically effective amount is an amount sufficient to reduce the symptoms of a polygenic disorder.

Dosage, toxicity and therapeutic efficacy of the compounds can be determined, e.g., by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred. While compounds that exhibit toxic side effects may be used, care should be taken to design a delivery system that targets such compounds to the site of affected tissue in order to minimize potential damage to other tissue and organs and, thereby, reduce side effects.

Data obtained from cell culture assays or animal studies can be used in formulating a range of dosage for use in humans. If the pharmaceutical is provided systemically, the dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration or within the local environment to be treated in a range that includes the IC50 (i.e., the concentration of the test compound that achieves a half-maximal inhibition of neoplastic growth) as determined in cell culture. Such information can be used to more accurately determine useful doses in humans. Levels in plasma may be measured, for example, by liquid chromatography coupled to mass spectrometry.

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a composition depends on the composition selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the compositions described herein can include a single treatment or a series of treatments. For example, several divided doses may be administered daily, one dose, or cyclic administration of the compounds to achieve the desired therapeutic result.

A number of medications and treatments are known for several polygenic disorders, especially those that arise due to underlying and/or related factors. Accordingly, embodiments are directed toward treating an individual with a treatment regime and/or medication when diagnosed with a polygenic disorder as described herein. Various embodiments are directed to treatments of polygenic (i.e., multifactorial) disorders and/or components thereof, including (but not limited to) Alzheimer's disease, arthritis, asthma, coronary artery disease, Crohn's disease, dementia, diabetes, heart disease, heart failure, cholesterol imbalance, hypertension, hypothyroidism, irritable bowel syndrome, obesity, Parkinson's disease, psoriasis, sleep apnea, and stroke. It is to be understood that a number of polygenic disorders are also components of another disorder and vice versa, as is typical for complex disorders as described herein.

Once diagnosed for having a risk of Alzheimer's disease, neurological and neuropsychological tests can be performed to check mental status. Imaging (e.g., MRI, CT, and PET) can be performed to check for abnormalities in structure or function. A number of supplements may help brain health and may be prophylactic, including (but not limited to) omega-3 fatty acids, curcumin, ginkgo, and vitamin E. Exercise, diet, and social support can help promote good cognitive health. Medications for Alzheimer's include (but are not limited to) cholinesterase inhibitors and memantine.

Once diagnosed for having a risk of arthritis, laboratory tests on various bodily fluids can be performed to determine the type of arthritis. Imaging (e.g., X-rays, CT, MRI, and ultrasound) can be utilized to detect problems in various joints. Physical therapy may help relieve some complications associated with arthritis. Medications for arthritis include (but are not limited to) analgesics, nonsteroidal anti-inflammatory drugs (NSAIDs), counterirritants, disease-modifying antirheumatic drugs, biologic response modifiers, and corticosteroids. Heat pads, ice packs, acupuncture, glucosamine, yoga, and massage are examples of various home/alternative remedies available.

Once diagnosed for having a risk of asthma, tests can be performed to determine lung function. A chest X-ray or CT scan can be performed to determine any structural abnormalities. Medications for asthma include (but are not limited to) inhaled corticosteroids, leukotriene modifiers, long-acting beta agonists, short-acting beta agonists, theophylline, and ipratropium. In some instances, allergy medications may help asthma and thus allergy shots and/or omalizumab can be administered. Regular exercise and maintaining a healthy weight may help reduce asthma symptoms.

Once diagnosed for having a risk of coronary artery disease, an electrocardiogram and/or echogram can be performed to determine a heart's performance. A stress test can be performed to determine the ability of the heart to respond to physical activity. A heart scan can determine whether calcium deposits exist. Patients having risk of coronary artery disease would benefit greatly from a few lifestyle changes, including (but not limited to) reduce tobacco use, eat healthy foods, exercise regularly, lose excess weight, and reduce stress. Various medications can also be administered, including (but not limited to) cholesterol-modifying medications, aspirin, beta clockers, calcium channel blockers, ranolazine, nitroglycerin, ACE inhibitors and angiotensin II receptor blockers. Angioplasty and coronary artery bypass can be performed when more aggressive treatment is necessary.

Once diagnosed for having a risk of Crohn's disease, a combination of tests and procedures can be performed to confirm the diagnosis, including (but not limited to) blood tests and various visual procedures such as a colonoscopy, CT scan, MRI, capsule endoscopy and balloon-assisted enteroscopy. Treatments for Crohn's disease includes corticosteroids, oral 5-aminosliclates, azathioprine, mercaptopurine, infliximab, adalimumab, certolizumab pegol, methotrexate, natalizumab and vedolizumab. A special diet may help suppress some inflammation of the bowel.

Once diagnosed for having a risk of dementia, further analysis of mental function can be performed to gauge memory, language skills, ability to focus, ability to reason, and visual perception. These analyses can be performed utilizing cognitive and neuropsychological tests. Brain scan (e.g., CT, MRI, and PET) and laboratory tests can be performed to determine if physiological complications exist. Medications for dementia include cholinesterase inhibitors and memantine.

Once diagnosed for having a risk of diabetes/glycemia, a number of tests can be performed to determine an individual's glucose levels and regulation, including (but not limited to) glycated hemoglobin A1C test, fasting blood sugar levels, and oral glucose tolerance test. Routine visits may be performed to get a long-term regulatory look at glucose regulation. In addition, a glucose monitor can be utilized to continuously monitor glucose levels. Diabetes can be managed by various options, including (but not limited to) healthy eating, regular exercise, medication, and insulin therapy. Medications for diabetes include (but are not limited to) metformin, sulfonylureas, meglitinides, thiazolidinediones, DPP-4 inhibitors, SGLT inhibitors, and insulin.

Once diagnosed for having a risk of heart disease, various tests can be performed to determine heart function, including (but not limited to) electrocardiogram, Holter monitoring, echocardiogram, stress test, and cardiac catheterization. Lifestyle changes can dramatically improve heart disease, including (but not limited to) limiting tobacco products, controlling blood pressure, keeping cholesterol in check, keeping blood glucose levels in a good range, physical activities, eating healthy, maintaining a healthy weight, managing stress, and coping with depression. A number of medications can be provided, as dependent on the type heart of disease.

Once diagnosed for having a risk of heart failure, various tests can be performed to confirm the diagnosis, including (but not limited to) physical exams, blood tests, chest X-rays, electrocardiogram, stress test, imaging (e.g., CT and MRI), coronary angiogram, and myocardial biopsy. Medications for heart failure include (but are not limited to) ACE inhibitors, angiotensin II receptor blockers, beta blockers, diuretics, aldosterone antagonists, inotropes, and digoxin. Surgical procedures may be necessary, and include (but are not limited to) coronary bypass surgery and heart valve repair/replacement.

Once diagnosed for having a risk of cholesterol imbalance, blood tests can be performed to measure total cholesterol, LDL cholesterol, HDL cholesterol, and triglycerides. Medications to manage cholesterol levels include (but are not limited to) statins, bile-acid-binding resins, cholesterol absorption inhibitors, and fibrates. Supplements can also be taken, including (but not limited to) co-enzyme Q, red yeast rice extract, niacin, soluble fiber, and omega-3-fatty acids. Individuals at risk for high cholesterol should also reduce tobacco products, eat a healthy diet (avoiding saturated fat, trans fat, and salt), and get regular exercise.

Once diagnosed for having a risk of hypertension, blood pressure levels can be monitored periodically (even at home). Elevated blood pressure and hypertension benefit from lifestyle changes including, eating healthy, reducing sodium intake, regular physical activity, maintaining a proper rate, and limiting alcohol intake. Medications for hypertension include (but are not limited to) ACE inhibitors, angiotensin II receptor blockers, calcium channel blockers, alpha blockers, beta blockers, aldosterone antagonists, renin inhibitors, vasodilators, and central-acting agents.

Once diagnosed for having a risk of hypothyroidism, blood tests can be performed to measure the level of TSH and thyroid hormone thyroxine. Medications for hypothyroidism includes (but is not limited to) synthetic thyroid hormone levothyroxine, which may be taken with supplements such as iron, aluminum hydroxide, and calcium to help absorption.

Once diagnosed for having a risk of irritable bowel syndrome (IBS), physical exams can be performed to confirm IBS including determining type of IBS. These exams include (but are not limited to) flexible sigmoidoscopy, colonoscopy, X-ray, and CT scan. A proper diet can be utilized to manage symptoms, including (but not limited to) high fiber fluids, plenty of fluids, and avoiding the following: high-gas foods, gluten, and FODMAPs. Medications for IBS include (but are not limited to) alosetron, eluxadoline, rifaximin, lubiprostone, linaclotide, fiber supplements, laxatives, anti-diarrheal medications, anticholinergic medications, antidepressants, and pain medications.

Once diagnosed for having a risk of obesity, a physiological test to determine body-mass index (BMI) may be performed. Obesity can be managed by various lifestyle remedies including (but not limited to) healthy diet, physical activity, and limiting tobacco products. If obesity is severe, various surgeries can be performed, including (but not limited to) gastric bypass surgery, laparoscopic adjustable gastric banding, biliopancreatic diversion with duodenal switch, and gastric sleeve.

Once diagnosed for having a risk of Parkinson's disease, a single-photon emission computerized tomography (SPECT) scan can image dopamine transporter activity in the brain, which can be monitored over time. Medications for Parkinson's includes (but are not limited to) carbidopa-levodopa, dopamine agonists, MAO B inhibitors, COMT inhibitors, anticholinergics and amantadine.

Once diagnosed for having a risk of psoriasis, routine physical exams of the skin, scalp and nails can be performed to look for signs of inflammation. A number of topical treatments can be performed for psoriasis, including (but not limited to) topical corticosteroid, vitamin D analogues, anthralin, topical retinoids, calcineurin inhibitors, salicylic acid, coal tar, and moisturizers. A number of phototherapies can also be performed, including (but not limited to) exposure to sunlight, UVB phototherapy, Goeckerman therapy, excimer laser, and psoralen plus ultraviolet A therapy. Medications for psoriasis include (but are not limited to) retinoids, methotrexate, cyclosporine, and biologics that reduce immune-mediated inflammation (e.g., entanercept, infliximab, adalimumab).

Once diagnosed for having a risk of multiple sclerosis (MS), various tests can be performed overtime to monitor symptoms of MS, including (but not limited to) blood tests, lumbar puncture, MRI and evoked potential tests. A number of treatments can help treat acute MS symptoms and to mitigate MS progression, including (but not limited to) corticosteroids, plasma exchange, ocrelizumab, beta interferons, glatiramer acetate, dimethyl fumarate, fingolimod, teriflunomide, natalizumab, alemtuzumab, and mitoxantrone. Physical therapy and muscle relaxants also help mitigate (or prevent) MS symptoms.

Once diagnosed for having a risk of sleep apnea, an evaluation that monitors an individual's sleep may be performed, including (but not limited to) nocturnal polysomnography, measurements of heart rate, blood oxygen levels, airflow, and breathing patterns. Sleep apnea therapy may include the use of a continuous positive airway pressure (CPAP) device or bilevel positive airway pressure (BiPAP or BPAP). A number of lifestyle changes have also been shown to mitigate complications associated with sleep apnea, including (but not limited to) losing excess weight, physical activity, mitigating alcohol consumption, and sleeping on side or abdomen.

Once diagnosed for having a risk of stroke, routine monitoring can be performed to determine coronary health status, including (but not limited to) blood clotting tests, imaging (e.g., CT and MRI) to look for potential clots, carotid ultrasound, cerebral angiogram, and echocardiogram. Various procedures that can be performed include (but are not limited to) carotid endarterectomy and angioplasty. Patients having risk of stroke would benefit greatly from a few lifestyle changes, including (but not limited to) reduce of tobacco use, eat healthy foods, exercise regularly, lose excess weight, and reduce stress. Various medications can also be administered, including (but not limited to) cholesterol-modifying medications, aspirin, beta clockers, calcium channel blockers, ranolazine, nitroglycerin, ACE inhibitors and angiotensin II receptor blockers.

EXEMPLARY EMBODIMENTS

The embodiments of the invention will be better understood with the several examples provided within. Many exemplary results of computational models to predict polygenic risk scores from genetic data are described. Description of medical disorders and the weight of their subcomponent phenotypes as determined from genetic data are also described.

Example 1: Polygenic Risk Modeling with Latent Trait-Related Genetic Components

Common diseases like diabetes and heart disease are leading causes of death and financial burden in the developed world. Polygenic risk scores (PRS), which sum the contributions of multiple risk loci toward phenotypes of interest, have been used with some success to identify individuals at high risk for common diseases like cancer, diabetes, heart disease, and obesity. Although many versions of PRS can be used to estimate risk, a "palette" model which decomposes genetic risk into its constituent pathways may more faithfully describe the clinical manifestations of complex disease.

Figure 2:
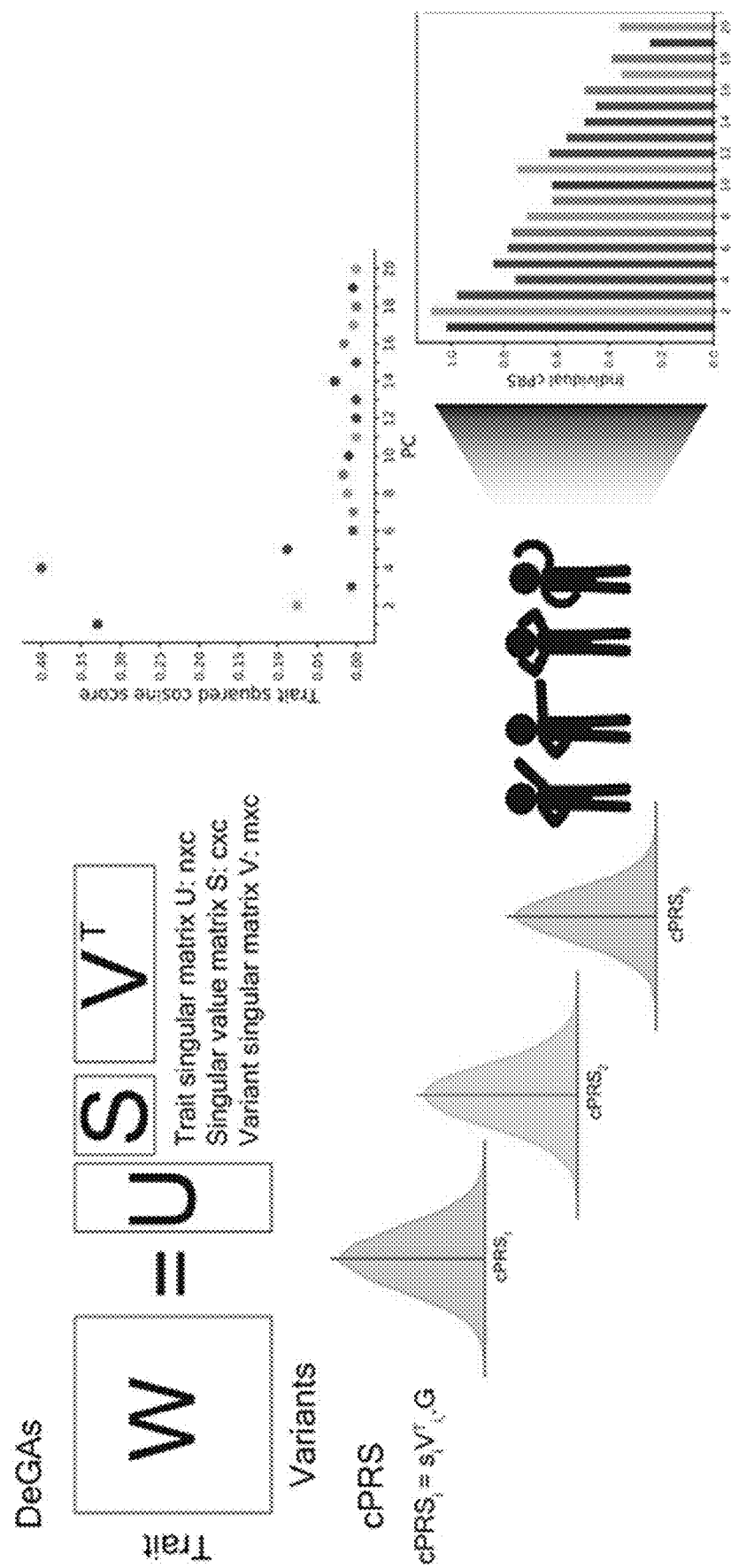
FIG. 2 provides an example of matrix decomposition of genetic associations (DeGAs), which is performed by taking the truncated singular value decomposition (TSVD) of a matrix W (n×m) containing summary statistics from GWAS of n=977 traits over m=469,341 variants from the UK Biobank, utilized in accordance with various embodiments. The squared columns of the resulting singular matrices U (n×c) and V (m×c) measure the importance of traits (variants) to each component; the rows map traits (variants) back to components. The squared cosine score (a unit-normalized row of US) for some hypothetical trait indicates high contribution from PC1, PC4, and PC5.
Figure 3:
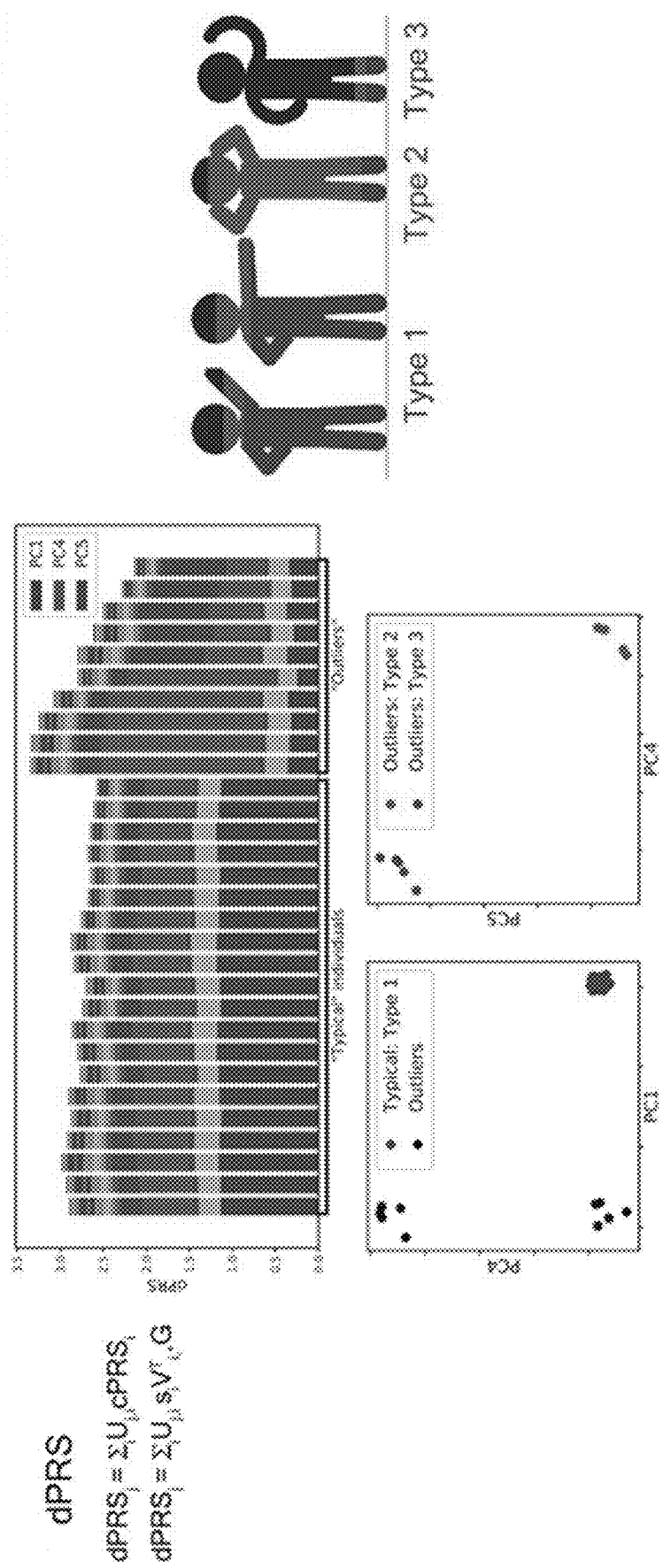
FIG. 3 provides an example of DeGAs polygenic risk scores (dPRS) for trait j, recovered by taking a weighted sum of $cPRS_i$, with weights from U (j,i-th entry), utilized in accordance with various embodiments. DeGAs risk profiles are computed for each individual, which measure the relative contribution of each component to genetic risk. The dPRS high risk individual is "painted" with these profiles and labeled "typical" or "outlier" based on similarity to the mean risk profile (driven by PC1, in blue). Outliers are clustered on their profiles to find additional genetic subtypes: this identifies "Type 2" and "Type 3", with risk driven by PC4 (red) and PC5 (tan). Clusters visually separate each subtype along relevant cPRS (below).

This example describes a polygenic model based on latent trait-related genetic components identified using Decomposition of Genetic Associations (DeGAs). Rather than modeling genetic risk for a trait as a sum of effects from contributing genetic variants, the DeGAs polygenic risk score (dPRS) models genetic risk for traits as a sum of contributions from DeGAs components. Each component consists of a set of variants which affect a subset of the traits being modeled (FIGS. 2 and 3). Genetic risk for an individual DeGAs component can be expressed as a component PRS (cPRS) that approximates risk for a weighted combination of relevant traits. These scores are used to estimate personalized genetic risk profiles that inform genetic subtyping of disease.

As proof of concept, DeGAs was computed using summary statistics generated from genome-wide associations between 977 traits and 469,341 independent common variants in a subset of unrelated white British individuals (n=236,005) in the UK Biobank (C. Bycroft, et al., Nature 562, 203-209 (2018), the disclosure of which is incorporated herein by reference). A series of dPRS models was developed and their performance was evaluated in independent samples of unrelated individuals in the same population (n=33,716 validation set; n=67,430 test set), and in UK Biobank non-British whites (n=25,486 additional test set). Results for body mass index (BMI), myocardial infarction (MI/heart attack), and gout, are provided, motivated by their high prevalence (obesity, in the case of BMI) among older individuals in this cohort.

Methods

Study Populations

The UK Biobank is a large longitudinal cohort study consisting of 502,560 individuals aged 37-73 at recruitment during 2006-2010. The data acquisition and study development protocols are online (www.ukbiobank.ac.uk/wp-content/uploads/2011/11/UK-Biobank-Protocol.pdf). In short, participants visited a nearby center for an in-person baseline assessment where various anthropometric data, blood samples, and survey questionnaire responses were collected. Additional data were linked from registries and collected during follow-up visits.

A subsample consisting of 337,151 unrelated individuals of white British ancestry was used for genetic analysis. We split this cohort at random into three groups: a 70% training population (n=236,005), a 10% validation population (n=33,716), and a 20% test population (n=67,430). The training population was used to conduct genome-wide association studies for DeGAs and the validation population to evaluate model performance for selecting DeGAs hyperparameters. Final associations and performance measures in the test population are reported within. An additional cohort of unrelated non-British White individuals (n=25,486) was used as an additional independent evaluation set. The "white British" and "non-British white" populations were defined using a combination of genotype PCs from UK Biobank's PCA calculation and self-reported ancestry (UK Biobank Field 21000).

In brief, individuals were subject to the following filtration criteria from the UK Biobank sample quality control file (ukb_sqc_v2.txt): "putative sex chromosome aneuploidy=0", "het_missing_outliers=0", "excess_relatives=0", and "used_in_pca_calculation=1". Individuals were labeled "white" based on two thresholds in Biobank's PCA calculation: $-20<=PC1<=40$ and $-25<=PC2<=10$. Individuals in the "non-British white" were set as those that self-reported white but not British ancestry in Field 21000. The "white British" set was taken to individuals with "in_white_British_ancestry_subset=1" in the sample quality control file.

Genome-Wide Association Studies in the UK Biobank:

PLINK v2.00a (C. C. Chang, et al., Gigascience 4, 7 (2015), the disclosures of which is incorporated herein by reference) [2 Apr. 2019] was used for genome-wide associations of 805,426 directly genotyped variants, 362 HLA allelotypes, and 1,815 non-rare (AF>0.01%) copy number variants (CNV) in the UKB training population. The —glm Firth-fallback option was used to apply an additive-effect model across all sites. Quantitative trait values were inverse-transformed by rank to a normal distribution using the— pheno-quantile-normalize flag. The following covariates were used: age, sex, the first four genetic principal components, and, for variants present on both of the UK Biobank's genotyping arrays, the array which was used for each sample.

Prior to public release, genotyped sites and samples were subject to rigorous quality control by the UK Biobank. In brief, markers were subject to outlier-based filtration on effects due to batch, plate, sex, genotyping array, as well as discordance across control replicates. Samples with excess heterozygosity (thresholds varied by ancestry) or missingness (>5%) were excluded from the data release. Prior to use in downstream methods, additional variant quality control was performed on array-genotyped variants, including more stringent filters on missingness (>1%), gross departures ($p<10^{-7}$) from Hardy-Weinberg Equilibrium, and other indicators of unreliable genotyping. As with previous versions of DeGAs, variants were further filtered by minor allele frequency (MAF>0.01%), array-specific missingness (<5%), and LD-independence. The LD independent set was computed with "—indep-pairwise 50 5 0.5" in PLINK v1.90b4.4 [21 May 2017]. MAF and LD filters were applied within and across each array-genotyped group. This process resulted in a set of 469,341 variants (467,427 genotyped variants, 118 HLA allelotypes, and 1,796 CNVs) for the analysis.

Binary disease outcomes were defined from UK Biobank resources using combining self-reported questionnaire data and diagnostic codes from hospital inpatient data. Additional traits like biomarkers, environmental variables, and self-reported questionnaire data like health outcomes and lifestyle measures were collected from fields curated by the UK Biobank and processed. Multiple observations were processed by taking the median of quantitative values, or by defining an individual as a binary case if any recorded instance met the trait's defining criteria. In all, we collected 977 traits with at least 1000 observations (quantitative traits) or cases (binary traits). These comprise most common traits in the Global Biobank Engine, excluding imaging features and those which were subject to manual curation. In this work, results for body mass index (GBE ID: INI21001), myocardial infarction (HC326), and gout (HC328) are highlighted, although the methods incorporated can be applied to any multifactorial trait.

Risk Modeling Using Decomposition of Genetic Associations (DeGAs)

Figure 4:
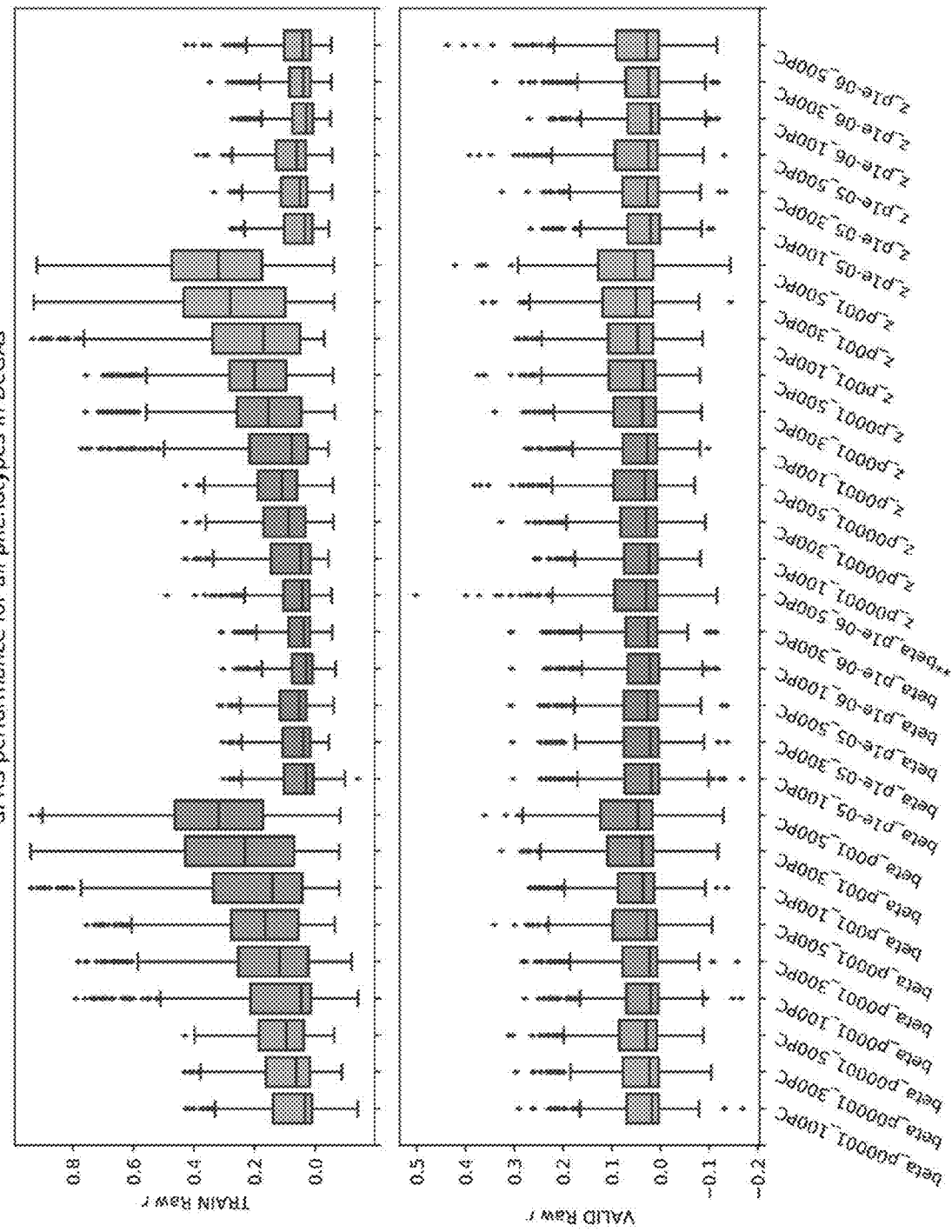
FIG. 4 provides a data graph of hyperparameter optimization, utilized in accordance with various embodiments. Distribution of Spearman's rho between trait dPRS and trait values (top, in the training set; bottom, in the validation set) for all traits in several DeGAs models. We computed DeGAs across an array of parameters, varying input statistics (betas or z-statistics) from GWAS; minimum p-value filters (p=1e-2, 1e-3, 1e-4, 1e-5, 1e-6); and the number of components to compute (c=100,300,500). The model with optimal performance was chosen by maximizing mean rho between dPRS and trait in the validation set (bottom). It used z-statistics from associations with p<1e-2 and 300 components and is labeled with two stars (**).

Given summary statistics from GWAS computed using the above methods, matrix Decomposition of Genetic Associations (DeGAs) was performed. First, a sparse matrix of genetic associations W (n×m) was assembled using effect size estimates (or z-statistics) between n=977 traits and m=469,341 non-rare variants (MAF>0.01%). Only variants with at least 2 nominally significant associations were used ($p<10^{-6}$; FIG. 4 has additional cutoffs). After filtration, input statistics were standardized to zero mean and unit variance within each trait so as to weigh them equally relative to one another.

Subsequently, a truncated singular value decomposition (TSVD) was performed on W using the Truncated SVD function in the scikit-learn python module (F. Pedregosa, et al., J. Mach. Learn. Res. 12, 2825-2830 (2011) and N. Halko, et al, SIAM Review 53, 217-288 (2011), the disclosure of which are each incorporated herein by reference) to identify the top c=500 trait-related genetic components. This factorization results in three matrices whose product approximates W: a trait singular matrix U (n×c), a variant singular matrix V (m×c), and a diagonal matrix S (c×c) of singular values, which was denoted $s_i$ for the i-th component (FIG. 2). With TSVD, W is approximated by U, S, and V using the below:

$$w = USV^T$$

The matrices U, S, and V are then used to compute component polygenic risk scores (cPRS). The component PRS for the i-th DeGAs component can be written as $$cPRS_i = S_{i,*} V^T G$$

for an individual with genotype vector G (m×1) over the variants used in DeGAs. Here, $S_{i,*}$ denotes the i-th row of S. Using the cPRS for each component, the DeGAs polygenic risk score (dPRS) for the j-th trait can be defined as $$dPRS_j = \Sigma_i U_{j,i} cPRS_i$$

where $U_{j,i}$ is the (j,i)'th entry of U. In terms of the matrices U, S, and V, this can be expressed as $$dPRS_j = U_{j,*} SV^T G$$

For interpretability, the population distribution of dPRS for each trait j is scaled to zero mean and unit variance, independent of the distributions of dPRS for other traits.

Individuals were further related to traits via components using a measure referred to herein as the DeGAs risk profile (dRP). An individual's profile for a given phenotype j is a vector over the c DeGAs components, where the value for the i-th component is proportional to $$dRP_{j,i} \sim \max(0, dPRS_j \times cPRS_i)$$

with a denominator introduced for normalization so that these values sum to one. To estimate the contribution of each component to an individual's overall genetic risk, only component scores which have the same sign as the overall risk score was considered (hence the max operator). This gives normalized risk profiles consisting of driving components for high risk individuals with positive dPRS and protective components for low risk individuals with negative dPRS.

Computing Polygenic Risk Scores

As a baseline model for dPRS, single-trait polygenic risk scores (PRS) was computed with a pruning and thresholding approach using the same summary statistics used as input to DeGAs. These variants were already filtered on LD independence and for $p<p*$ based on a critical value $p*$ (see above), so no further processing was required. For a given DeGAs instance, the weights for prune- and threshold PRS for trait j were taken from the j-th row of W. The PRS was then computed with PLINK v1.90b4.4 [21 May 2017] using the—score flag, with the 'sum', 'center', and 'double-dosage' modifiers. These correspond to the assumptions that variants make additive contributions across sites; the mean distribution of risk is taken to be zero; and that the effect alleles have additive effects; these are also the same assumptions used in the input GWAS.

In a similar fashion, polygenic scores (cPRS) for all DeGAs components were computed with PLINK2 v2.00a2 (2 Apr. 2019) using the—score flag, with 'center' and 'cols=scoresums' modifiers. These modifiers correspond to the same assumptions as in the PRS: that genetic effects are additive across sites (this is the default genotype model for—score); each component is zero-centered; and alleles make additive contributions. Given population-wide estimates of cPRS for every component, we computed dPRS and DeGAs risk profiles for each trait using the above formulas.

Optionally, PRS and dPRS were adjusted by age, sex, and four genetic principal components from UK Biobank's PCA calculation. Adjustment was performed by fitting a multiple regression model with dPRS (or PRS) and covariates in the 10% validation population. A covariate-only was also fit model using the same procedure (without either polygenic score) and use its performance as a baseline for the joint models (FIG. 5).

Model Validation

Figure 6:
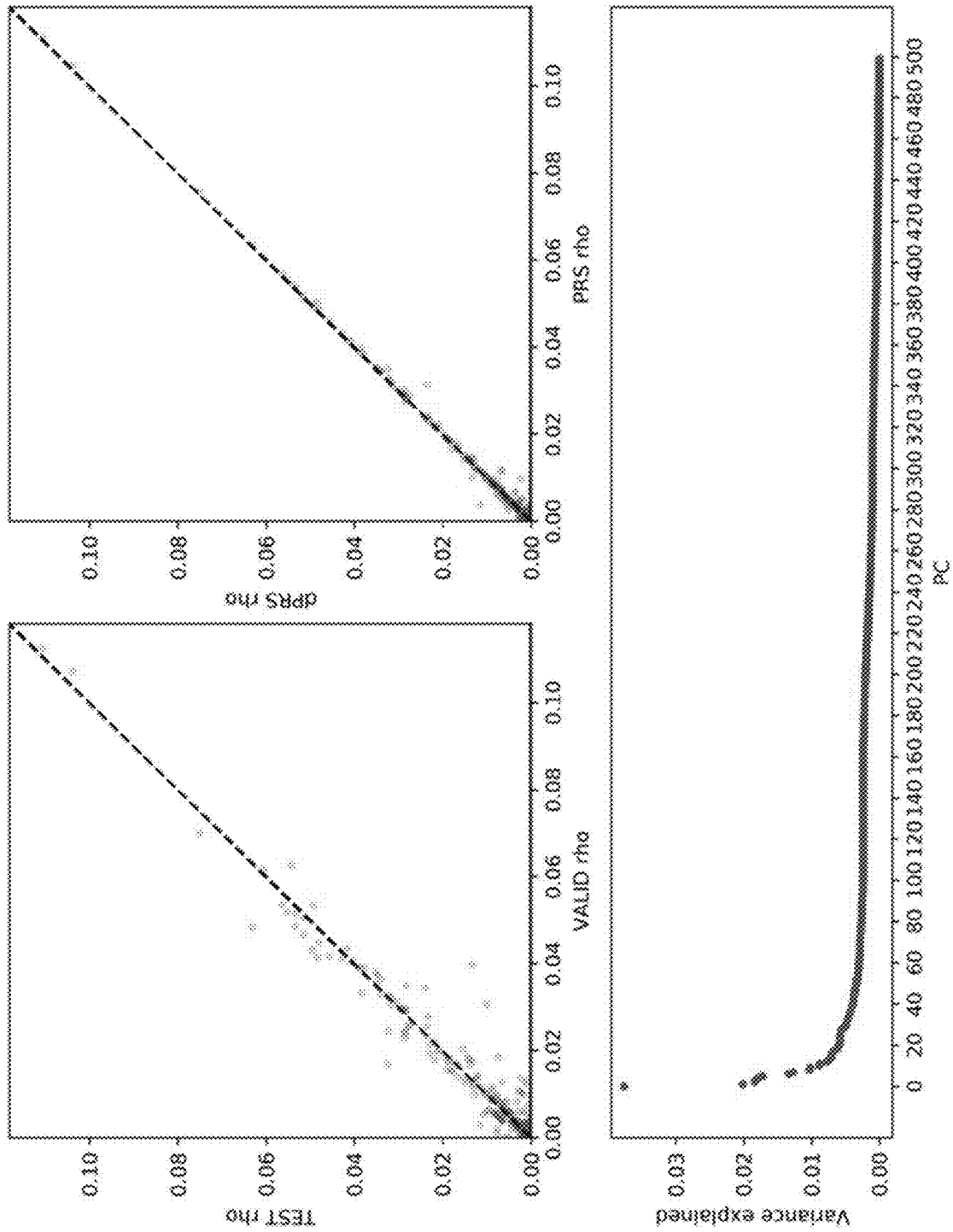
FIG. 6 provides data graphs depicting performance of the final DeGAs model with optimized hyperparameters, utilized in accordance with various embodiments. Squared rank correlation (Spearman's rho) was plotted between dPRS and trait values across all traits in the test (top left) and validation sets (top left), or between dPRS and PRS in the test set (top right). The fraction of variance explained by each DeGAs component is shown in a scree plot (bottom). These c=500 components collectively explain ~99.9% of variance in the original input matrix.

To select DeGAs hyperparameters (the input p-value filter, and whether to use GWAS betas or z-statistics as weights) a grid search was performed over a range of filtering p-values for both betas and z-statistics. Performance of a DeGAs instance was assessed using the average correlation between its dPRS models and their respective traits. For all traits used in the decomposition, Spearman's rho (rank correlation) was computed between dPRS and covariate-adjusted trait residuals in the training and validation sets. Residual traits are the result of regressing out age, sex, and four genetic principal components. To avoid overfitting, modest correlation (Pearson's $r^2>0.5$) was required between training and validation set performance. This constraint provided optimal performance using betas, a p-value cutoff of $10^{-6}$, and 500 components (FIG. 4). This model explains nearly all (>99%) of the variance of its corresponding input matrix W (FIG. 6).

Figure 5:
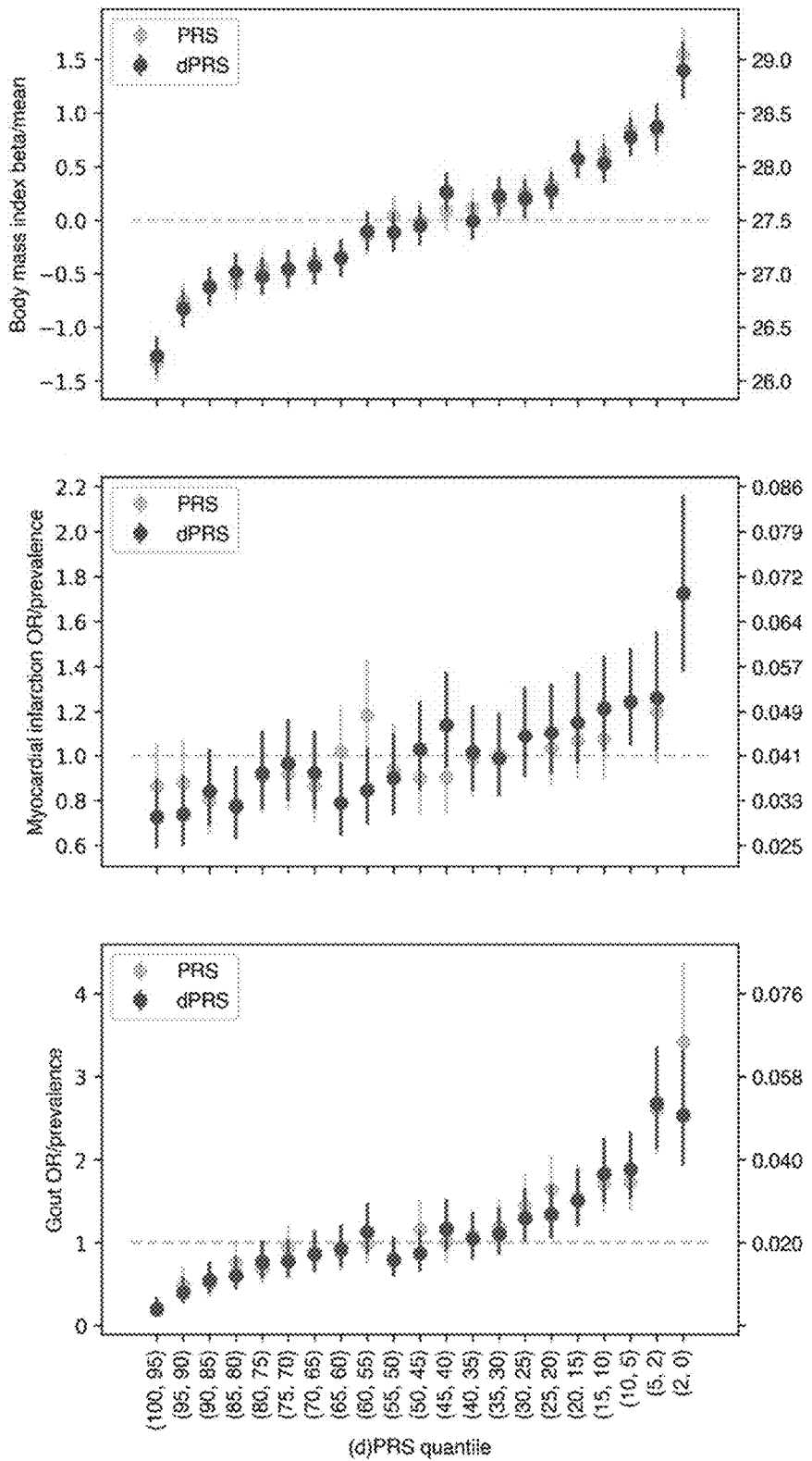
FIG. 5 provides data graphs depicting performance of dPRS, utilized in accordance with various embodiments. Effect of increased risk (dPRS or PRS) on BMI, MI, and gout. Beta/OR (left axis) were estimated by comparing the quantile of interest (x-axis) with a middle quantile (40-60%), adjusted for these covariates: age, sex, 4PCs. Trait mean or prevalence (right axis) was computed within each quantile; error bars denote the 95% confidence interval of each estimate.

For this best-performing DeGAs instance, several assessment metrics for each polygenic score—dPRS and PRS with DeGAs input data—within each study population was utilized (FIG. 5). For each score and population, disease prevalence and mean quantitative trait values was estimated at various population risk strata. The effect of dPRS (or PRS) quantiles on traits was also estimated using a two-step approach. First, in the training set, the following is computed:

$$Y \sim \beta_0 + \beta_1 sex + \beta_2 age + \sum_{i=1}^{4} \beta_{i+2} PC_i$$

Then, in the test/validation set the effect β due to PRS quantile is estimated using the above parameters like so:

$$Y \sim \hat{\beta}_0 + \hat{\beta}_1 sex + \hat{\beta}_2 age + \sum_{i=1}^{4} \hat{\beta}_{i+2} PC_i + \beta 1_{PRS(q)}$$

where $1_{PRS(q)}$ is an indicator function that equals 1 if an individual is in the quantile of interest q (e.g. 0-2%), and 0 if the individual is in the baseline group (40-60% risk quantile). Individuals in neither the quantile of interest nor the baseline group were excluded; if individuals were in both q and the baseline group (e.g. if q were 45-40%) they were counted in q and removed from baseline.

The scores' ability to predict quantitative trait values and perform binary classification on disease status was assessed. For quantitative traits, Pearson's r between score and trait residuals were determined, as defined above. For binary traits, the area under the receiver operating curve (AUROC/AUC) was determined with dPRS as the classifying score, both alone and in a joint model with covariates. As baseline, AUC for a covariate-only model was also determined (see above).

Classifying Genetic Risk Profiles from DeGAs Components

In order to assess whether the method could identify subtypes of genetic risk, the DeGAs risk profiles of high risk individuals whose dPRS is driven by an "atypical" combination of DeGAs components was analyzed. The Mahalanobis distance (DM) was used to identify outlier individuals whose z-scored distance from the mean DeGAs risk profile exceeded 1:

$$D_M = \sqrt{(x-\mu)S^{-1}(x-\mu)^T}$$

where x is the DeGAs risk profile; μ is the mean profile; and S is the identity matrix. Traditionally, S is taken to be the covariance matrix for each of the features across all x's: each of the components is modelled as having equal variance so as to identify "atypical" individuals rather than statistical outliers. This formula reduces to the Euclidean distance between a DeGAs risk profile x and the mean profile μ.

Figure 15:
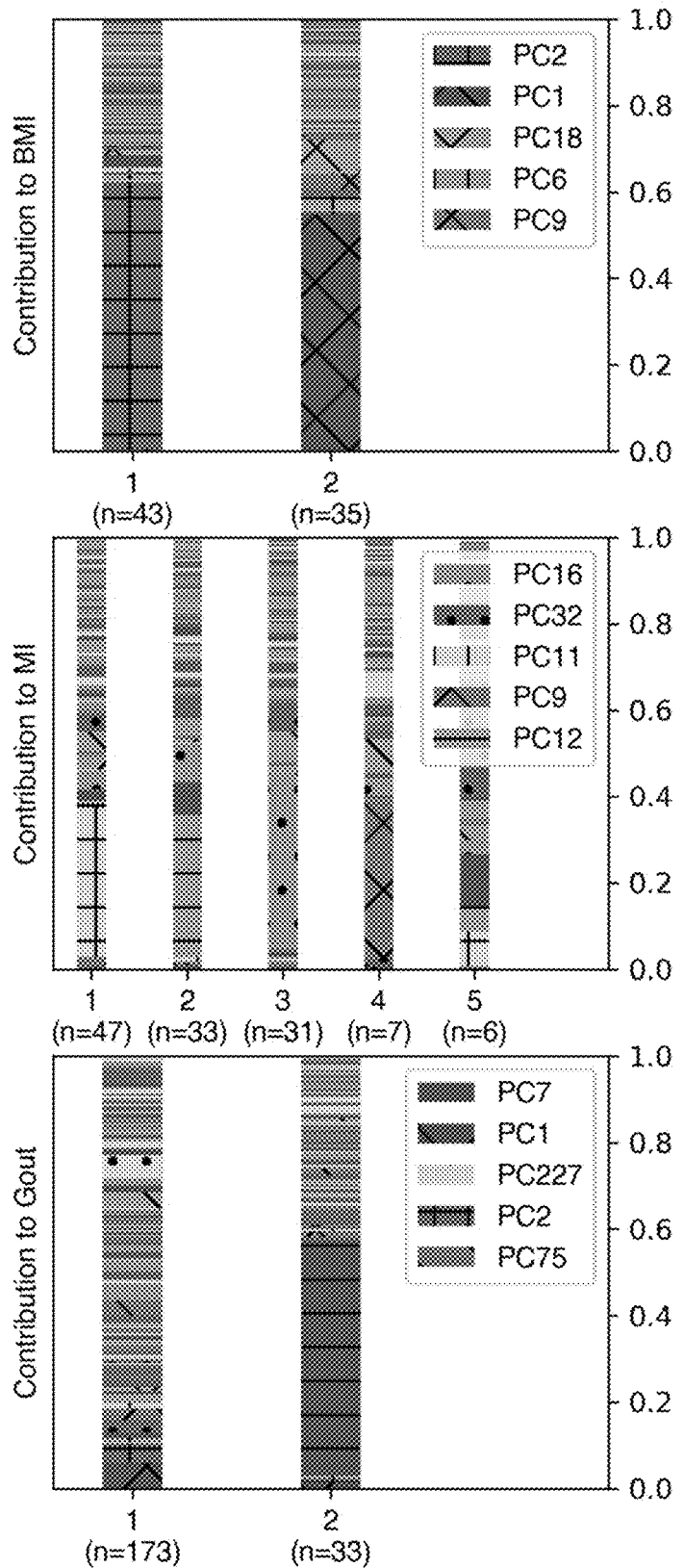
FIG. 15 provides mean DeGAs risk profiles from k-means clustering of high risk outlier risk profiles, annotated with cluster size (n), utilized in accordance with various embodiments. Phenotype groups for selected components in this figure include: PC1 (Fat free mass); PC2 (Fat mass); PC7 (Alcohol use); PC9 (leukocytes and viral antigens); PC11 (Lung function); PC12 (Aspirin and cholesterol medication); PC16 (Blood pressure medication); PC32 (Hearing, ibuprofen, and cholesterol medication).

This set of outlier individuals was intersected with the top 5% of dPRS to create the "high risk outlier" group. In this example, the mean risk profile for a trait was defined as the component-wise mean across all individuals' DeGAs risk profiles in a high risk set (top 5% of dPRS). To identify subtypes among high risk outliers, a k-means clustering of their DeGAs risk profiles was performed using the KMeans function from the python scikit-learn module (F. Pedregosa (2011), cited supra). The number of clusters k was determined by optimizing a modified gap statistic over putative values of k ranging from 1 to 20 using the gap-star statistic in the python "gap-statistic" module (R. Tibshirani, et al., Journal of the Royal Statistical Society: Series B (Statistical Methodology) 63, 411-423 (2001), the disclosure of which is incorporated herein by reference). The various components in each cluster were assessed to determine which components drove risk by computing a mean risk profile for the group (defined as above) and renormalized it to one for visualization (FIG. 15).

Results

Evaluating the DeGAs Polygenic Risk Score (dPRS):

Genome-wide associations between 977 traits and 469,341 independent human leukocyte antigen (HLA) allelotypes, copy-number variants, and array-genotyped variants were computed in a training set of 236,005 unrelated white British individuals from the UK Biobank study. DeGAs was applied to scaled beta- or z-statistics from these GWAS with varying p-value thresholds for input (FIG. 2). Polygenic risk scores for each DeGAs component was defined (cPRS, FIG. 2) and used them to build the DeGAs polygenic risk score (dPRS; FIG. 3). The model with optimal out-of-sample prediction (FIG. 4) corresponded to DeGAs on beta values with significant (p<10-6) associations.

To validate this model, disease prevalence was estimated (or, for BMI, mean BMI) at several quantiles of risk in a held-out test set of white British individuals in the UK Biobank (n=67,430). For all traits, the results showed increasing severity (quantitative) or prevalence (binary) at increasing quantiles of dPRS (FIG. 5) adjusted for age, sex, and the first 4 genotype principal components from UK Biobank's PCA calculation 16. This trend was most pronounced at the highest risk quantile (2%) for each trait. Results at this stratum were 1.40 kg/m2 higher BMI (95% CI 1.14-1.67); 1.73-fold increased odds of MI (CI: 1.38-2.16); and 2.53-fold increased odds of gout (CI: 1.93-3.33) over the population average in the test set (overall n=67,235 individuals for BMI; 2,812 MI cases; and 1,484 gout cases).

Figure 7:
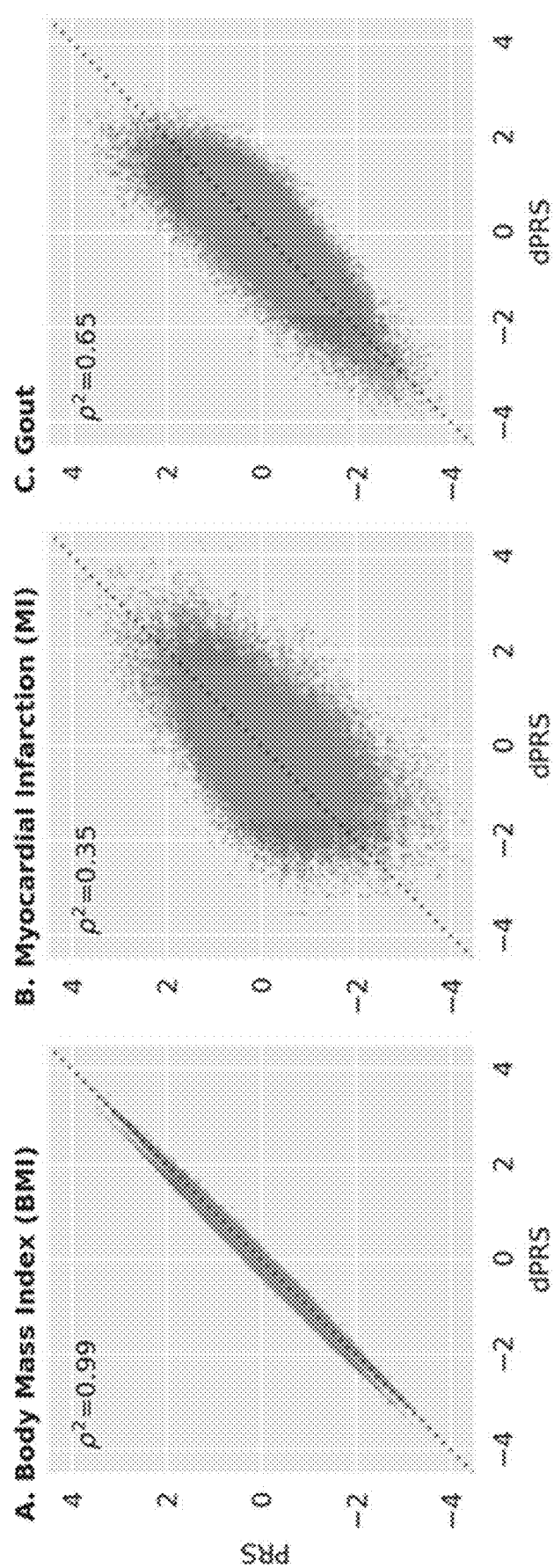
FIG. 7 provides data graphs depicting correlation between dPRS and PRS, utilized in accordance with various embodiments. For BMI (A), MI (B), and gout (C), dPRS (x-axis) and PRS (y-axis) for all individuals in the test set are shown alongside rank correlation (Spearman's rho squared) between the two. The gray diagonal line is y=x. Color represents whether the individuals are identified as high risk (top 5%) or low risk (bottom 5%) by dPRS, PRS, or both.
Figure 8:
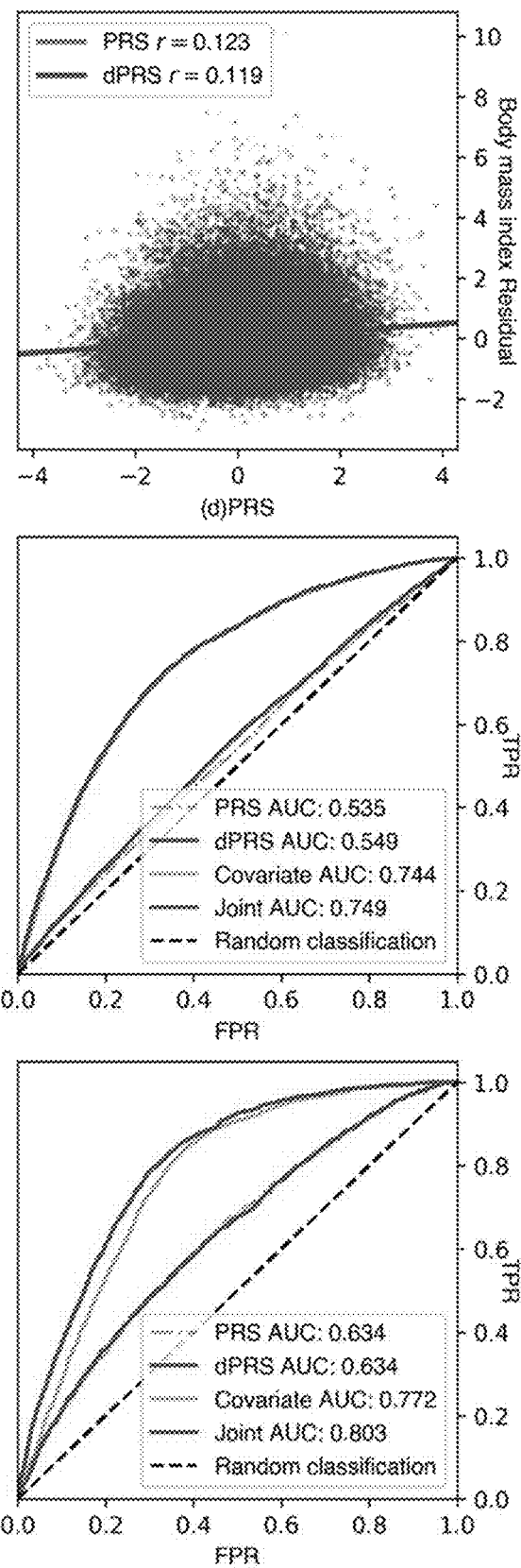
FIG. 8 provides data graphs depicting correlation between dPRS or PRS and covariate adjusted BMI, utilized in accordance with various embodiments.
Figure 9:
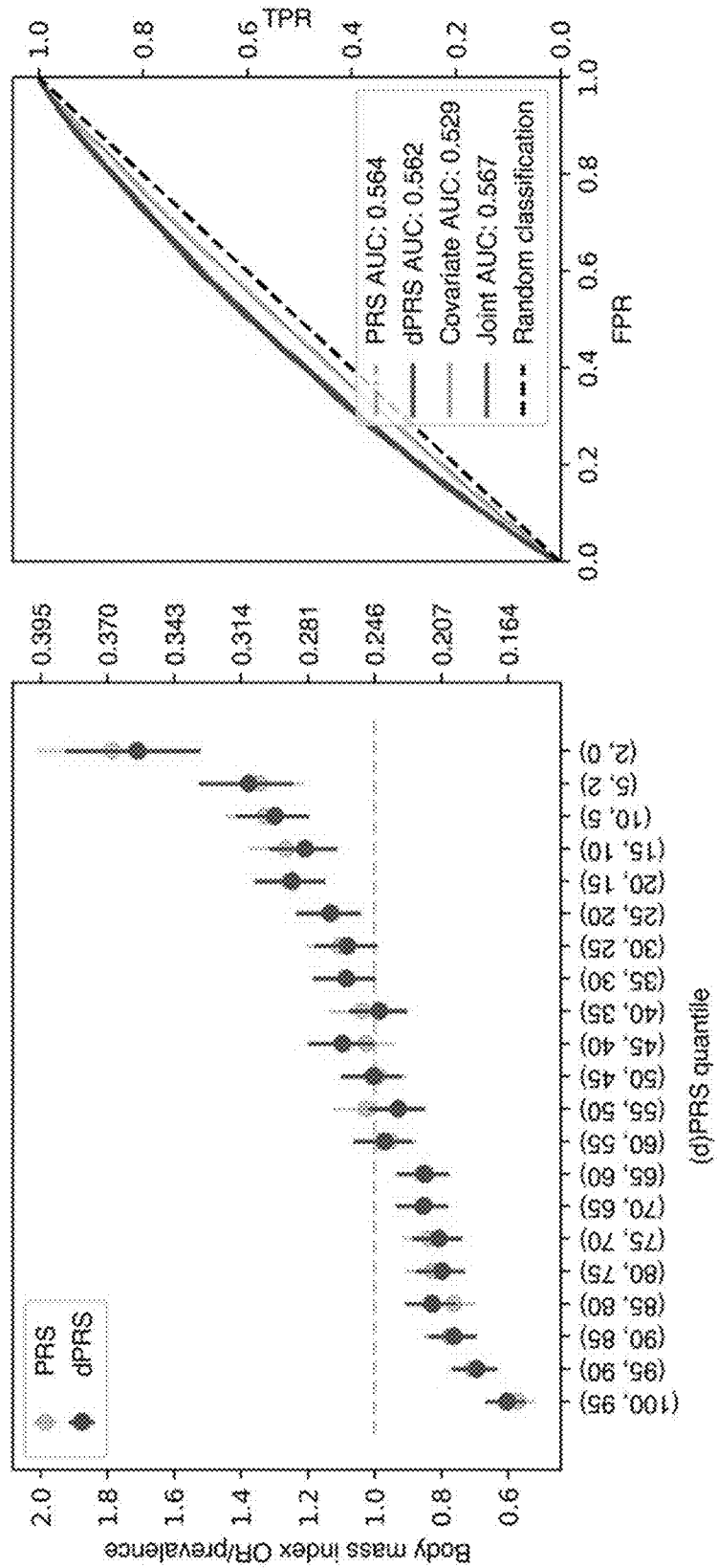
FIG. 9 provides data graphs depicting BMI dPRS/PRS performance predicting obesity, utilized in accordance with various embodiments. ORs at various risk quantiles were estimated by comparing the quantile of interest (x-axis) with a middle quintile (40-60%), adjusted for these covariates: age, sex, 4PCs. Trait prevalence (right axis) was computed within each quantile; error bars denote the 95% confidence interval of each estimate. Receiver operating curves with area under curve (AUC) values for BMI dPRS, PRS, covariates, and a joint model with covariates and dPRS. Models with covariates were fit in the validation set; all evaluation was in the test set. The second percentile of risk for dPRS (PRS) in the test set of white British individuals has OR=1.71 (1.79) with 95% CI [1.52, 1.93] (1.59, 2.01).

Further, dPRS is comparable to prune- and threshold-based PRS using the same input data (FIG. 6). Although there was some discrepancy between the individuals considered high risk by each model (FIG. 7, Table 1), similar effects were observed at the extreme tail of PRS as with dPRS. The top 2% of risk of PRS for each trait had 1.54 kg/m$^2$ higher BMI (CI: 1.28-1.81); 1.72-fold increased odds of MI (CI: 1.38-2.16); and 3.42-fold odds of gout (CI: 2.67-4.38) (FIG. 5) using the same covariate adjustment as dPRS. Population-wide predictive measures were also similar, with BMI residual r=0.21, and PRS AUC (not adjusted for covariates) 0.54 for MI and 0.63 for gout (FIG. 8). The model performed similarly for BMI dPRS predicting obesity (defined as BMI>30; FIG. 9), with OR=1.7 at the 2% tail, and AUC=0.56. On balance, despite the reduced rank of the DeGAs risk models—the input matrix W is reduced from ~1,000 traits to a 500-dimensional representation—performance was equivalent to traditional PRS for these traits, and observe a similar trend for the other traits (FIG. 6).

However, it is noted that dPRS and PRS add comparatively little population-wide predictive value over factors such as age, sex, and demographic effects that are captured by genomic PCs (FIG. 8). At the population level, results revealed an r=0.12 between covariate-adjusted dPRS and residual BMI. For binary traits, an area-under receiver operating curve (AUC) was calculated to be 0.55 for MI and 0.63 for gout, using unadjusted dPRS as the classifying score. After adjustment for covariates, the marginal increase in AUC is modest: 0.005 for MI and 0.03 for gout.

Characterizing DeGAs Components

Figure 10:
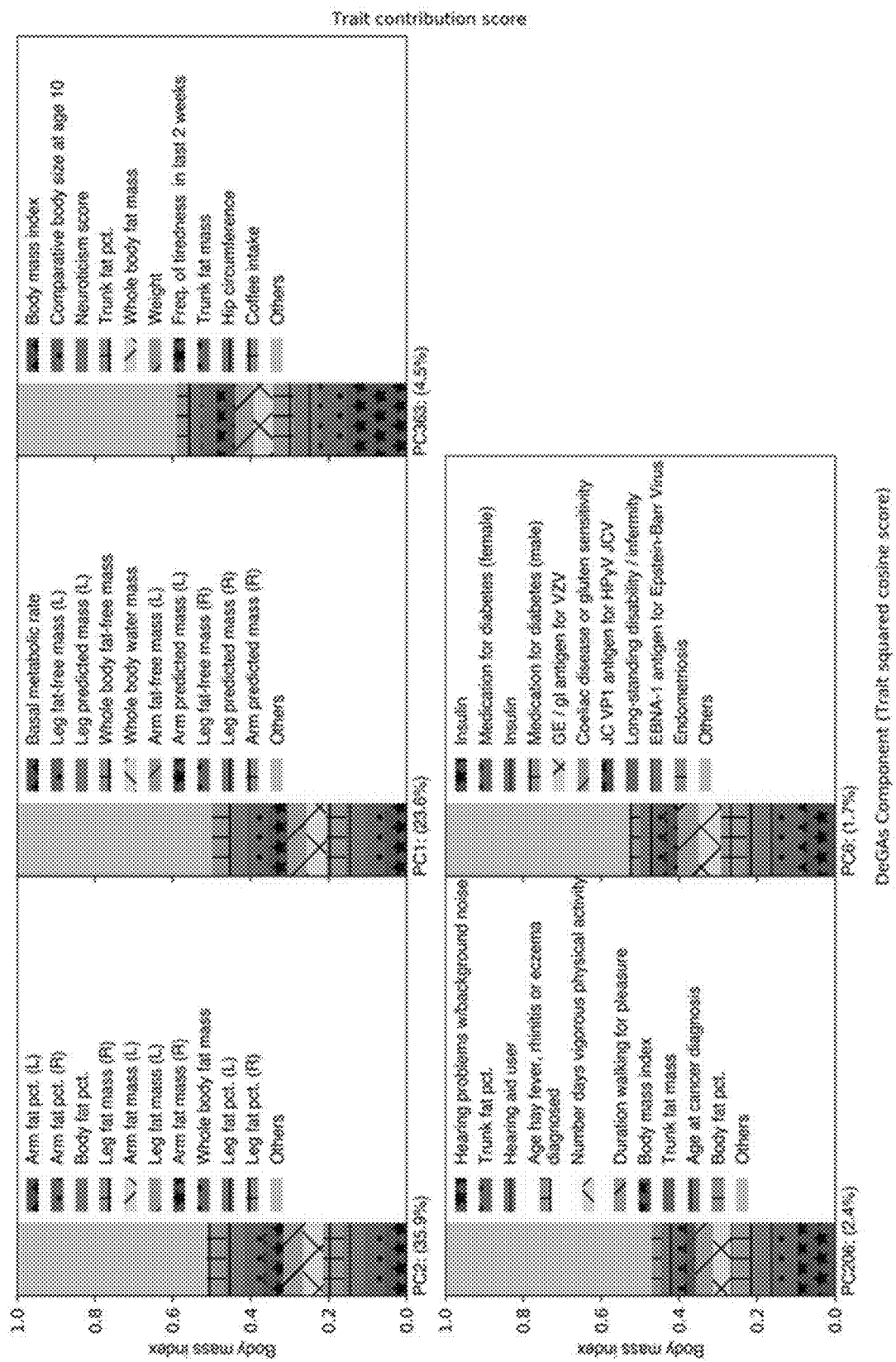
FIG. 10 provides an info graph depicting the top five DeGAs components for BMI, utilized in accordance with various embodiments. Top five DeGAs components for body mass index, as ranked by the trait squared cosine score. Each component is labeled with its top ten traits, as determined by the trait contribution score (squared column of U), and with its relative importance (squared cosine score). Traits are displayed for a component if their contribution score for the component exceeds 0.02.

The latent structure was identified through DeGAs by annotating each component with its contributing traits (FIG. 10) and variants, aggregated by gene. The relative importance of traits to components is measured using the trait contribution score, which corresponds to a squared column of the trait singular matrix U. The relative importance of components to each trait is measured using the trait squared cosine score, which is taken from a normalized squared row of US. These scores are defined analogously for variants and genes using the variant singular matrix V.

Body mass index is a highly polygenic trait with associated genetic variation relevant to adipogenesis, insulin secretion, energy metabolism, and synaptic function. Here, the DeGAs trait squared cosine score (FIG. 10) indicates strong contribution from components related to body size and fat-free mass (PC1; 23.6%), fat mass (PC2; 35.9%), as well as risk factors and comorbidities for obesity like body size at age 10 and trunk fat percentage (PC363; 4,5%). Components related to exercise (PC206=2.4%), and diabetes (PC6; 1.7%) also contribute.

Genetic variation proximal to STC2 (MIM: 603665) and MC4R (MIM: 155541) contribute strongly to both PC1 and PC2. STC2 is a stanniocalcin-related protein most highly expressed in cardiomyocytes and skeletal muscle. It has been associated with lean mass traits in humans and shown to restrict post-natal growth in mouse. MC4R is a melanocortin receptor in the G-protein coupled receptor family, is primarily expressed in the brain, and plays a role in energy homeostasis and somatic growth. It has been associated with fat-mass and obesity-related traits in humans. Both components further have contribution from variation proximal to FTO (MIM: 610966) and DLEU1 (MIM: 605765), which associate with traits affecting body size in adults. The former is an alpha-ketoglutarate dependent dioxygenase whose causal role in BMI has been questioned; the latter is a tumor-suppressing lncRNA named for its frequent deletion in patients with chronic lymphocytic leukemia.

Figure 11:
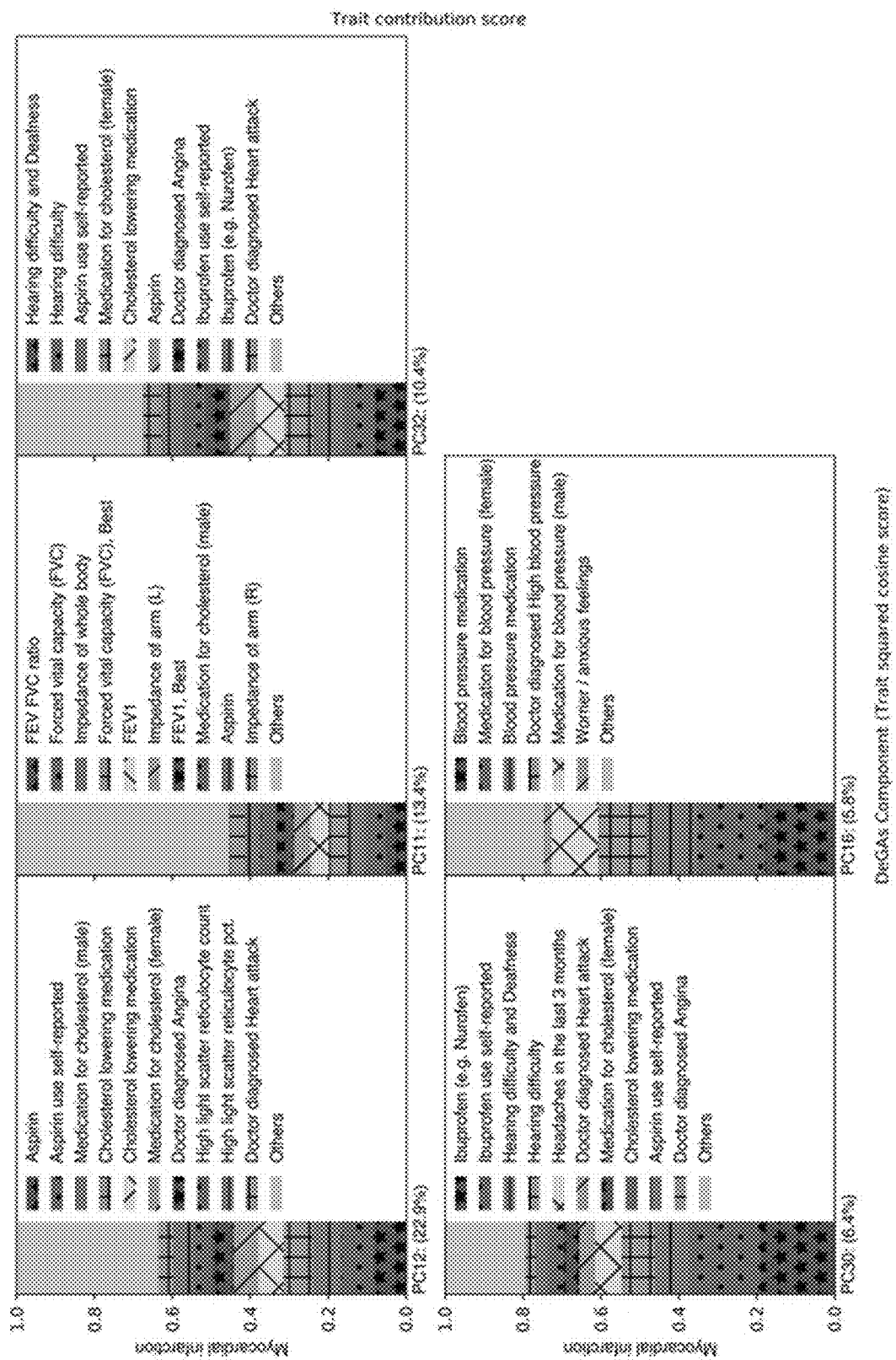
FIG. 11 provides an info graph depicting the top five DeGAs components for MI, utilized in accordance with various embodiments. Top five DeGAs components for myocardial infarction, as ranked by the trait squared cosine score. Each component is labeled with its top ten traits, as determined by the trait contribution score (squared column of U), and with its relative importance (squared cosine score). Traits are displayed for a component if their contribution score for the component exceeds 0.02.

Myocardial infarction is a polygenic outcome with well-established risk factors attributable to common and rare genetic variation, age, sex, and lifestyle attributes like diet and smoking. DeGAs components important to this trait are related to usage of an array of medications for comorbid conditions, as well as measures of lung function (FIG. 11). These medications include aspirin, ibuprofen, and cholesterol-lowering medications, which are represented across PC12 (22.9%; also includes reticulocytes), PC32 (10.4%; also includes hearing problems and angina), and PC30 (6.4%; also includes headaches). A component related to blood pressure medications also contributes (PC16-5.8%). Another relevant component (PC11-13.4%) has contribution from measures of lung function like forced expiratory volume in 1 second (FEV1), forced vital capacity (FVC), and the ratio of the two (FEV FVC ratio).

Two components, PC11 and PC12, have contribution from variation proximal to the lipoprotein gene LPA (MIM: 152200), at the 9p21.3 susceptibility locus (CDKN2B—MIM: 600431), and in the brain-expressed solute carrier SLC22A3[40] (MIM: 604842). Variation in all three of these genes also contributes to PC32, along with the transcription factor STAT6 (MIM: 601512), which has been associated with adult-onset asthma and inflammatory response to mosquito bites. PC30 also has contribution from this gene and the phosphatase and actin regulator PHACTRI (MIM: 618298), which has been identified in prior coronary artery disease GWAS.

Figure 12:
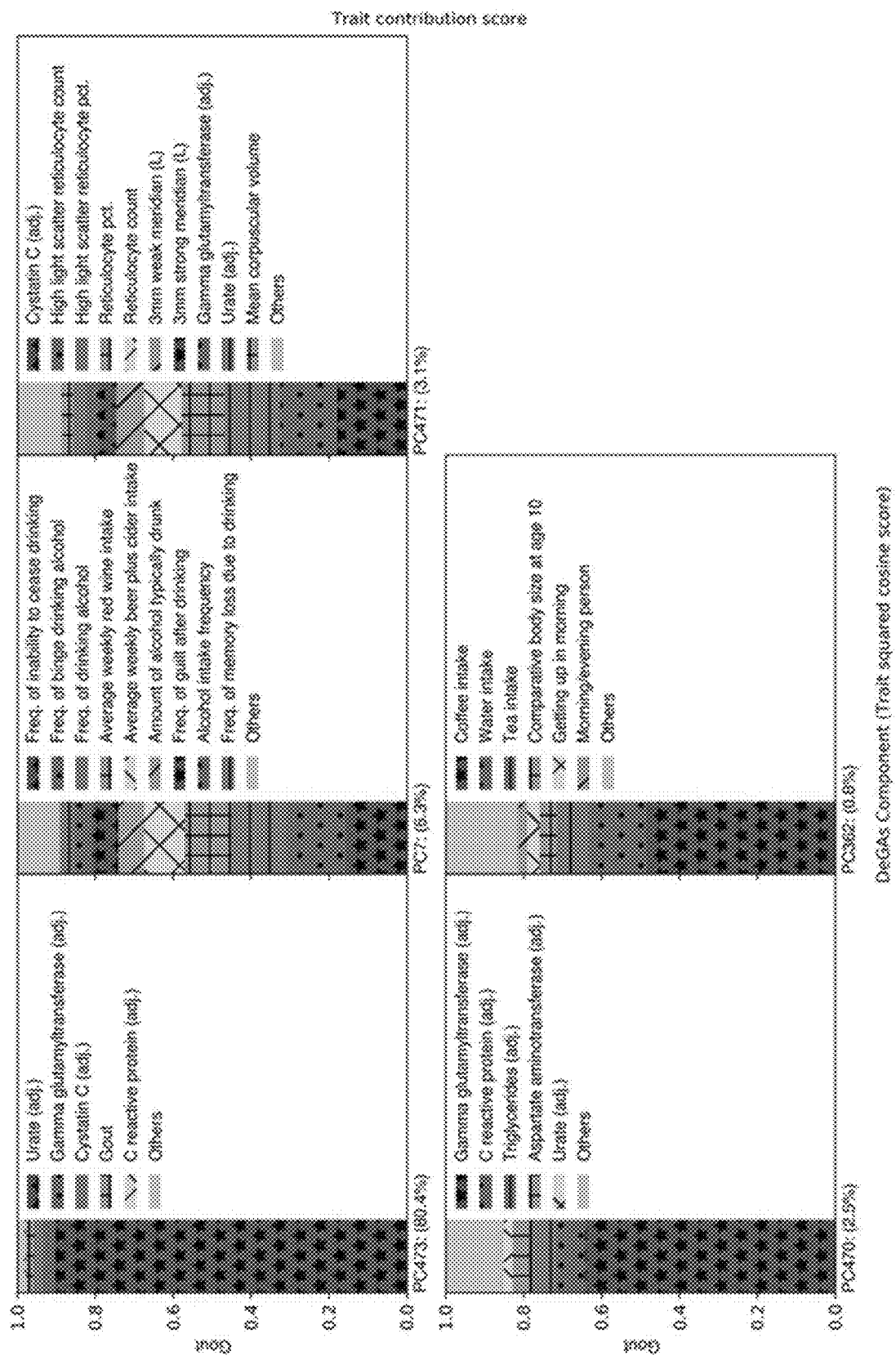
FIG. 12 provides an info graph depicting the top five DeGAs components for gout, utilized in accordance with various embodiments. Top five DeGAs components for gout, as ranked by the trait squared cosine score. Each component is labeled with its top ten traits, as determined by the trait contribution score (squared column of U), and with its relative importance (squared cosine score). Traits are displayed for a component if their contribution score for the component exceeds 0.02.

Gout is a heritable ($h^2$=17.0-35.1%) common complex form of arthritis characterized by severe sudden onset joint pain and tenderness, believed to arise due to excessive blood uric acid which crystallizes and forms deposits in the joints. The top component (FIG. 12) for gout has strong contribution from covariate-adjusted blood urate (PC473; 80.4%), which explains most variance in the input data. Two other components measure dietary intake, with one (PC7; 6.3%) is driven by measures of alcohol use and abuse; another (PC362; 0.8%) is related to coffee, water, and tea intake. Two other components are related to other covariate- and statin-adjusted biomarkers, namely cystatin C (PC471; 3.1%) and gamma glutamyltransferase (PC470; 2.5%). The key gene for PC473 is SLC2A9 (MIM: 606142), which is involved in uric acid transport and has been associated with gout. The alcohol dehydrogenase ADH1B (MIM: 603756) is further key to PC7, and is associated with alcoholism and blood urea nitrogen (BUN)[4][6], [4][7]. Indeed, alcohol use has been identified as a lifestyle risk factor for gout.

Painting DeGAs Risk Profiles

Figure 13:
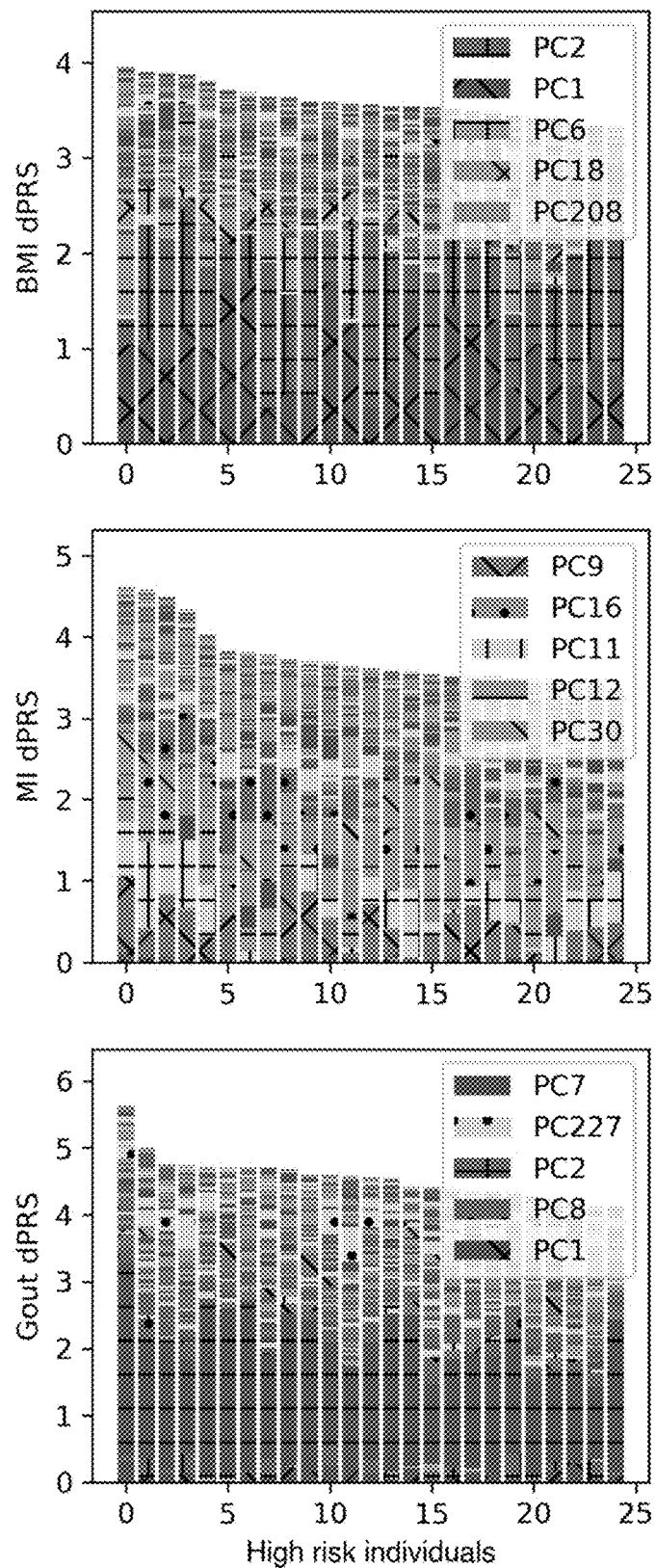
FIGS. 13 and 14 provide painting components of genetic risk, utilized in accordance with various embodiments. Component-painted risk for the 25 individuals (FIG. 13) or 25 outliers (FIG. 14) with highest dPRS for each trait in the test set. Each bar represents one individual; the height of the bar is the covariate-adjusted dPRS, and the colored components of the plot are the individual's DeGAs risk profile, scaled to fit bar height. Colors for the five most represented components in each box are shown in its legend in rank order.

To further characterize the architecture of genetic risk for these traits, the profiles of each high-genetic-risk individual (top 5% of dPRS) were "painted". For this, a person's genetic risk across DeGAs components was decomposed into a measure referred to in this example as the DeGAs risk profile. This captures relevant underlying genetic diversity among high risk individuals (FIG. 13) in a way which complements the population-level scores from DeGAs. For example, the trait squared cosine score for gout suggests that PC473 is the top component; but the DeGAs risk profile suggests PC7 (which has contribution from alcohol-related traits) has a key role in driving genetic risk at the extreme tail of dPRS for gout (FIG. 13).

The diversity of driving components among high risk individuals was investigated using their DeGAs risk profile. The Mahalanobis criterion was used to find individuals in the entire test population whose risk profiles significantly differed from average. These outliers (z-scored Mahalanobis distance >2) were then intersected with the high risk individuals (top 5% of dPRS) to identify "high risk outliers". This group (FIG. 14) has similar contributing components as the high risk individuals (FIG. 13), but their relative importance to each of the individuals is quite different. This suggests that the DeGAs risk profile, as a personalized measure, can identify individuals with high genetic risk who are poorly described by "typical" trait pathology.

Figure 14:
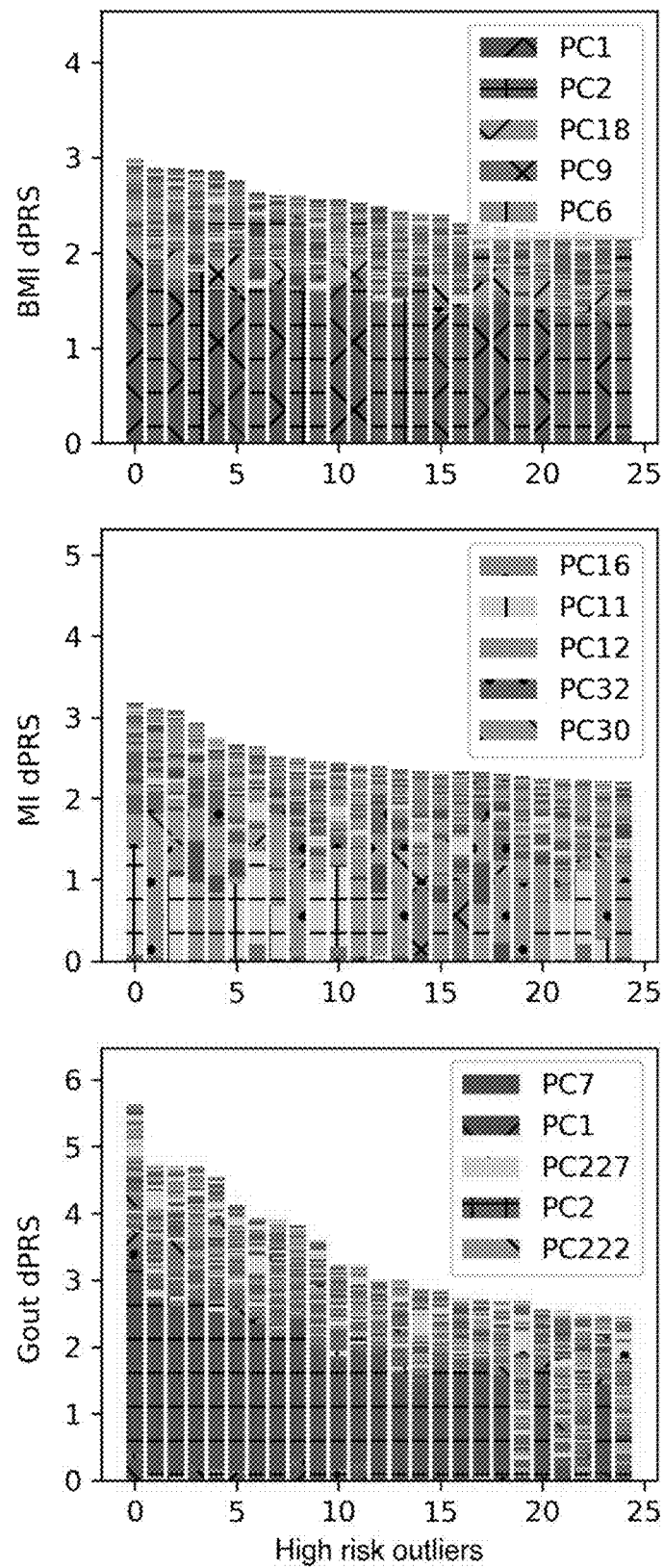

To better describe genetic diversity among these atypical individuals, there was an attempt to identify genetic subtypes of each trait in the high risk outlier population. A k-means clustering of this group was performed using DeGAs risk profiles as the input; k was chosen by optimizing the gap statistic across an array of potential values. Each cluster was described using its mean risk profile (FIG. 13). It was noticed that cluster membership divides individuals based on cPRS for relevant components (FIG. 14).

For body mass index, two risk clusters were identified (FIG. 15): one driven by the fat mass component (PC2-59.0%, n=43) and the other by the fat-free mass component (PC1-70.4%, n=35). Some outlying individuals at risk for high BMI have genetic contribution from the near exclusively fat-related component (PC2), hence their deviation from "typical". However, other individuals are outlying due to contribution from the lean mass component (PC1). Genetic risk from this cluster comes mainly from variant loadings related to fat-free mass-related traits like whole-body water and fat-free mass. The existence of this cluster and its wide separation from other outliers at risk for high BMI suggest alternative preventative and therapeutic approaches between the groups.

Five clusters of risk were identified for myocardial infarction (FIG. 15), four of which are driven primarily by components which were identified as important via the phenotype cosine score. These were PC11 (lung function; 34.8%; n=47), PC12 (high cholesterol; 32.9%; n=33), PC16 (blood pressure; 40.2%; n=31), and PC32 (hearing and cholesterol; 27.0%; n=6), all of which have strong contribution from medication use related to comorbid conditions (FIG. 15). The other cluster is driven primarily by PC9 (37.0%; n=7), which has high phenotype contribution from leukocyte measures, vitamin B9, and an array of viral antigens. Its genetic contribution is primarily from variants proximal to several HLA genes, and other genes in 6p21.3 like the butyrophilin-like protein BTNL2 (MIM: 606000) and the testis sperm-binding protein TSBP1 (MIM: 618151). Taken together these clusters could offer therapeutic insights, though the basis of each of the components is less clear to interpret than those underlying risk for BMI.

Two clusters of outliers were identified for gout (FIG. 15): one is driven by the alcohol trait component (PC7; 54.3%; n=33), and the other has a profile which does not have a single dominant component, and instead is driven by several (PC1, PC2, PC227; 6.0, 5.4, 5.5%; n=173). The cluster of outliers with risk driven by PC7 is not surprising, as the component is identified as important for gout by its trait cosine score. Further, genetic variation in ADH1B (one of the key genes for PC7) has been associated with gout, suggesting there may be shared genetic risk between both traits. The other cluster is harder to interpret, due to the number of relevant components.

Conclusions on Polygenic Risk Profiles

In this study, a novel approach to model polygenic traits using components of genetic associations is described. An example model was built using data from unrelated white British individuals in the UK Biobank to show that our method adds an interpretable dimension to traditional polygenic risk models by expressing disease, lifestyle, and biomarker-level elements in trait-related genetic components. Predicting genetic risk with these components led to an inference of disease pathology beyond variant-trait associations without loss of predictive power from reducing model rank (FIG. 6).

For three phenotypes of interest (BMI, MI, and gout), it was shown that the DeGAs risk profile offers meaningful insight into the genetic drivers of trait risk for an individual. This measure was then used to identify clusters of high risk individuals with similar genetic load for each of the traits. It was found that genetic risk for BMI can be decomposed into fat-mass and fat-free mass related components. It was also shown that while many individuals have risk for BMI driven by a combination of the two components, there exist "outlier" individuals who have strong contributions from only one of them. The results further indicate that this diversity of contributory genetic risk is not limited to BMI.

Figure 16:
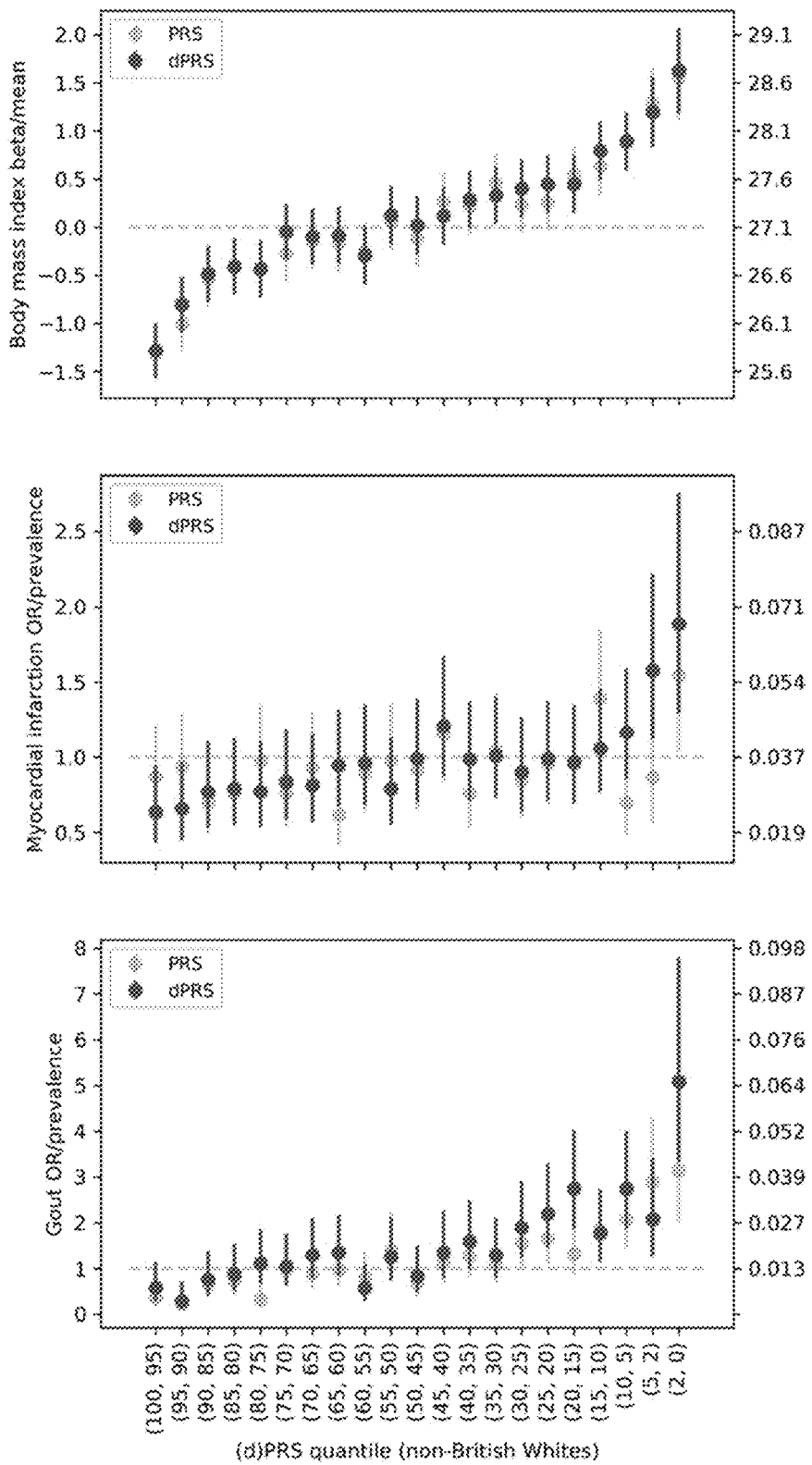
FIGS. 16 and 17 provide dPRS/PRS performance in non-British whites, utilized in accordance with various embodiments. The second percentile of risk for dPRS (PRS) has: 1.63 kg/m$^2$ (1.55) higher BMI, 1.89-fold (1.54) increased odds for MI, and 5.08-fold (3.15) increased odds of gout, adjusted for age, sex, and 4 genetic PCs. Overall model performance of dPRS (PRS) adjusted for these covariates is measured by Pearson's r for BMI or AUC for dPRS versus PRS alone, or dPRS+covariates versus a covariate model for the binary traits.
Figure 17:
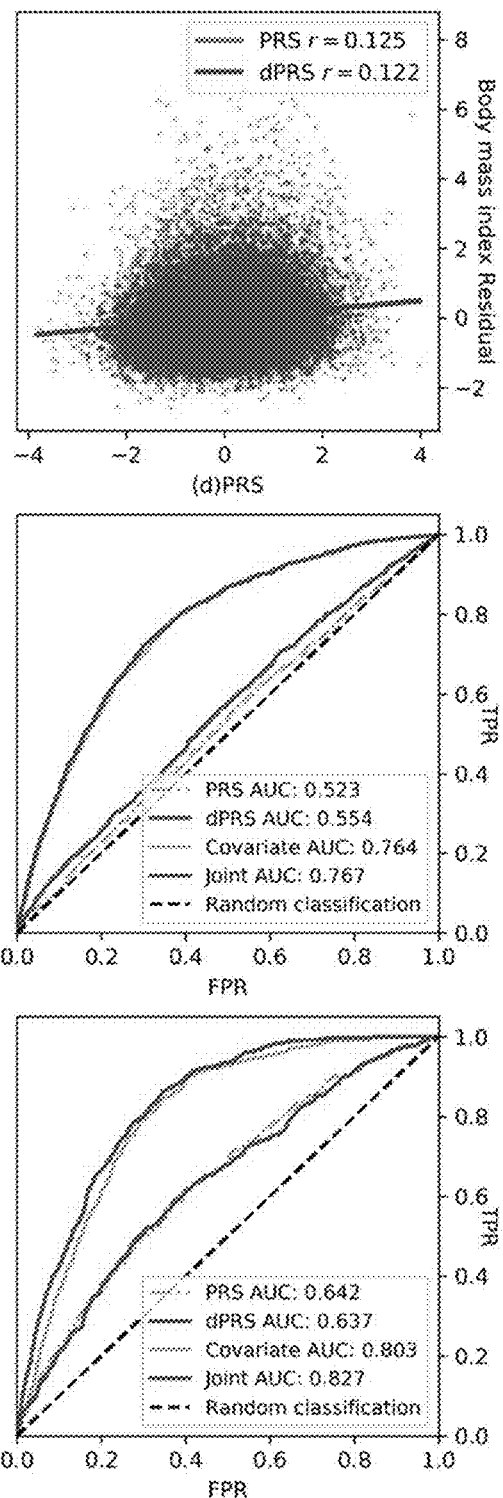

The generalizability of dPRS was demonstrated by assessing its performance in independent test sets of white British and non-British white individuals (FIGS. 16 and 17) from the UK Biobank. Among non-British whites, the top 2% of dPRS carries OR=1.9 for MI and 5.1 for gout (FIG. 16), compared to 1.7 and 2.5 in the test set individuals (FIG. 5). Likewise, the top 2% of dPRS risk has 1.63 $kg/m^2$ higher BMI in non-British whites (1.40 $kg/m^2$) in the test set. Though the performance was similar for these traits across these two groups, concerns about the generalizability of traditional clump-and-threshold PRS across groups also apply to dPRS. Though methods exist to identify suspected causal variants via fine-mapping, variants were LD-pruned prior to analysis with DeGAs. One benefit of this approach is that it is agnostic to patterns of association observed in GWAS for particular phenotypes.

It is also noted that the analysis of subtypes may not be robust to different choices of input traits or study population. Taking gout as an example, this study finds two clusters of outliers (FIG. 13), one of which is due to a component related to a clinical risk factor for the trait (namely, alcohol use). The ability to identify such clusters is clearly limited by the inclusion or exclusion of related traits and their degree of correlation in the analysis cohort. Here, traits which may have noisy or confounded patterns of genetic associations were excluded: specifically, rare conditions (n<1000 in the UK Biobank) or traits which correlate with social measures like socioeconomic status.

There are many applications of component-aware polygenic risk models like dPRS. Heritable conditions with known or putative biomarkers would be good candidates for follow-up studies that jointly investigate an outcome with its related features. Since DeGAs requires only summary-level data, it is possible to build a component model of genetic risk in one cohort (or across several) and use it to estimate genetic risk and identify trait subtypes in another. Such analyses will help elucidate the diversity of polygenic risk for complex traits across individuals and populations.

TABLE 1

Comparison of risk stratification by dPRS and PRS. For each BMI, MI, and gout, the number of individuals in the same (or different) risk strata were counted under each model. Binary cases and controls are further split ("phenotype" column) within each bin of risk for dPRS and PRS. Counts are shown for the top 5% (A) and bottom 5% (B).

| dPRS | PRS | BMI | MI | Gout | Phenotype |
|---|---|---|---|---|---|
| Top 5% | | | | | |
| Top 5% | Top 5% | 3165 | 91 | 87 | Case |
| | | | 1227 | 1257 | Control |
| | Bottom 95% | 196 | 109 | 88 | Case |
| | | | 1934 | 1936 | Control |
| Bottom 95% | Top 5% | 197 | 105 | 101 | Case |
| | | | 1936 | 1923 | Control |
| | Bottom 95% | 63677 | 2492 | 1203 | Case |
| | | | 59341 | 60640 | Control |
| Bottom 5% | | | | | |
| Bottom 5% | Bottom 5% | 3116 | 21 | 2 | Case |
| | | | 791 | 2064 | Control |
| | Top 95% | 251 | 82 | 12 | Case |
| | | | 2468 | 1281 | Control |
| Top 95% | Bottom 5% | 251 | 100 | 11 | Case |
| | | | 2447 | 1282 | Control |
| | Top 95% | 63617 | 2594 | 1454 | Case |
| | | | 58742 | 61129 | Control |

DOCTRINE OF EQUIVALENTS

While the above description contains many specific embodiments of the invention, these should not be construed as limitations on the scope of the invention, but rather as an example of one embodiment thereof. Accordingly, the scope of the invention should be determined not by the embodiments illustrated, but by the appended claims and their equivalents.

What is claimed is:

1. A diagnostic method to determine an individual's risk for and treatment of heart disease, comprising:
   obtaining genetic sequence data comprising genetic variants of an individual; and
   for a medical disorder (j), determining, using the variants within the sequence data, a component polygenic risk score for each component (i) of a set of components, wherein the medical disorder is heart disease, and
   wherein the set of component polygenic risk score is computed as follows:
      assembling a sparse matrix of genetic associations (W) between a set of traits (n) and a select set of variants (m) that are nominally significantly associated with at least one trait,
      identifying the set of components by performing truncated singular value decomposition on the matrix of genetic associations, resulting in three matrices that approximate the genetic association as follows: $W = USV^T$, wherein the three matrices are: a trait singular matrix U (n×c), a variant singular matrix V (m×c), and a diagonal matrix S (c×c) of singular values, and
      computing each component polygenic risk score (cPRS) as follows:
         $cPRS_i = S_{i,*} * V^T G$, wherein $S_{i,*}$ denotes the i-th row of S and G is the genotype vector G (m × 1) of the individual over the select set of variants;
   utilizing the set of component polygenic risk scores, determining a comprehensive polygenic score for the medical disorder by aggregating the set of component polygenic risk scores, wherein the comprehensive polygenic score indicates the individual is likely to have or to develop the medical disorder, and wherein the comprehensive polygenic risk score is computed as follows: $dPRS_j = \Sigma_i U_{j,i} cPRS_i$, wherein $U_{j,i}$ is the (j,i)'th entry of U;
   determining contribution of a number of components of the set of components, wherein contribution of at least one component indicates that the at least one component is a factor involved in manifestation of heart disease, wherein the at least one component is high glycemia, high cholesterol, high blood pressure, or obesity; and
   based on the comprehensive polygenic score and the contribution of at least one component, performing a treatment on the individual for heart disease, wherein the treatment is directed towards the at least one component that is a factor involved in manifestation of heart disease;
   wherein when the at least one component is high glycemia, the treatment is directed towards lowering high glycemia, wherein the step of performing a treatment on the individual for heart disease comprises administering a medication selected from: metformin, sulfonylureas, meglitinides, thiazolidinediones, DPP-4 inhibitors, SGLT inhibitors, and insulin;
   wherein when the at least one component is high cholesterol, the treatment is directed towards lowering high cholesterol, wherein the step of performing a treatment on the individual for heart disease comprises administering a medication selected from: statins, bile-acid-binding resins, cholesterol absorption inhibitors, and fibrates;
   wherein when the at least one component is high blood pressure, the treatment is directed towards lowering high blood pressure, wherein the step of performing a treatment on the individual for heart disease comprises administering a medication selected from: ACE inhibitors, angiotensin II receptor blockers, calcium channel blockers, alpha blockers, beta blockers, aldosterone antagonists, renin inhibitors, vasodilators, and central-acting agents; and
   wherein when the at least one component is obesity, the treatment is directed towards reducing obesity, wherein the step of performing a treatment on the individual for heart disease comprises administering a medication selected from: metformin, sulfonylureas, meglitinides, thiazolidinediones, DPP-4 inhibitors, SGLT inhibitors, and insulin.

2. The method of claim 1, wherein the components that assessed for contribution have the same sign as the comprehensive polygenic risk score.

3. The method according to claim 1 further comprising:
   obtaining or having obtained a biopsy from the individual;
   extracting or having extracted DNA from the biopsy; and
   sequencing or having sequenced the extracted DNA to yield the genetic sequence data.

4. The method according to claim 1, wherein the variants comprise at least one of: single nucleotide variants, insertions, deletions, copy number variants, or HLA alleles.

5. The method according to claim 1, wherein the number of components in the set of components is an integer between 50 and 500.

6. The method according to claim 5, wherein the number of components is 500.

7. The method according to claim 1, wherein each component polygenic risk score is computed by assuming variants make additive contributions.

8. The method according to claim 1, where each component polygenic risk score of the set of components is computed using genome wide association beta or z-statistics.

9. The method according to claim 1, wherein the comprehensive polygenic risk score is adjusted by age, sex, genetic principal components, or any combination thereof.

10. The method according to claim 9, wherein the adjustment is performed by fitting a multiple regression model with polygenic risk scores and covariates in a validation population.

11. The method according to claim 1, wherein the comprehensive polygenic risk score is above a threshold.

12. The method according to claim 11, wherein the threshold is determined empirically to capture a certain percentage of individuals having the medical disorder in a population.

* * * * *